United States Patent
Dixon et al.

(10) Patent No.: US 7,964,763 B2
(45) Date of Patent: Jun. 21, 2011

(54) OLIGOMERISATION OF OLEFINIC COMPOUNDS IN AN ALIPHATIC MEDIUM

(75) Inventors: John Thomas Dixon, Vanderbijlpark (ZA); Esna Killian, Sasolburg (ZA); Annette Bollmann, Henley-on-Klip (ZA); Richard Neil Walsh, Vanderbijlpark (ZA); Matthew James Overett, Johannesburg (ZA); Kevin Blann, Alberton (ZA); David Hedley Morgan, Sasolburg (ZA)

(73) Assignee: Sasol Technology (Pty) Limited, Johannesburg (ZA)

( * ) Notice: Subject to any disclaimer, the term of this patent is extended or adjusted under 35 U.S.C. 154(b) by 459 days.

(21) Appl. No.: 11/629,533

(22) PCT Filed: Jun. 13, 2005

(86) PCT No.: PCT/IB2005/051940
§ 371 (c)(1),
(2), (4) Date: Oct. 6, 2008

(87) PCT Pub. No.: WO2005/123633
PCT Pub. Date: Dec. 29, 2005

(65) Prior Publication Data
US 2011/0086991 A1  Apr. 14, 2011

(30) Foreign Application Priority Data
Jun. 18, 2004 (ZA) .................................. 2004/4841

(51) Int. Cl.
*C07C 13/18* (2006.01)

(52) U.S. Cl. ....................................................... 585/350
(58) Field of Classification Search ................... 585/350
See application file for complete search history.

(56) References Cited

U.S. PATENT DOCUMENTS

| | | | |
|---|---|---|---|
| 3,635,937 A | 1/1972 | Bauer et al. | |
| 3,676,523 A | 7/1972 | Mason | |
| 3,906,053 A | 9/1975 | Lanier | |
| 6,096,676 A * | 8/2000 | Murray | ......................... 502/117 |
| 6,184,428 B1 | 2/2001 | Zahoor et al. | |
| 2002/0177744 A1 | 11/2002 | Small et al. | |

FOREIGN PATENT DOCUMENTS

| | | | |
|---|---|---|---|
| EP | 0121965 | * | 10/1984 |
| WO | WO 00/21970 | * | 4/2000 |
| WO | WO-02/04119 | | 1/2002 |
| WO | WO-03/053890 | | 7/2003 |
| WO | WO-03/053891 | | 7/2003 |
| WO | WO-2004/056477 | | 7/2004 |
| WO | WO-2004/056478 | | 7/2004 |
| WO | WO-2004/056479 | | 7/2004 |

* cited by examiner

Primary Examiner — Ling-Siu Choi
Assistant Examiner — Sonya Wright
(74) Attorney, Agent, or Firm — Finnegan, Henderson, Farabow, Garrett & Dunner, L.L.P.

(57) ABSTRACT

This invention relates to a process for producing an oligomeric product by the oligomerization of at least one olefinic compound by contacting the at least one olefinic compound with an oligomerization catalyst in an aliphatic liquid medium at a reaction temperature of at least 50° C. The catalyst comprises the combination of a source of a transition metal; and a ligating compound of the formula $(R^1)_m X^1 (Y) X^2 (R^2)_m$.

28 Claims, 1 Drawing Sheet

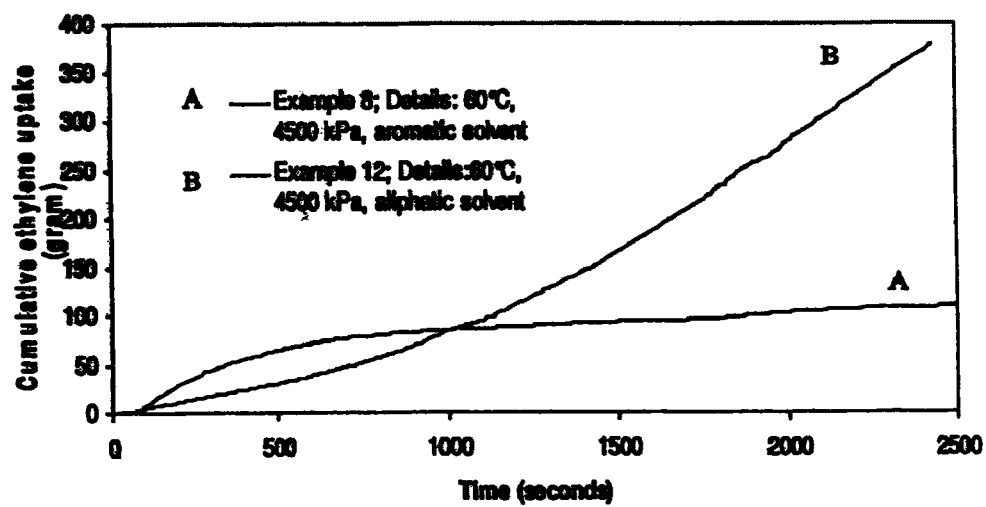
Figure 1: Cumulative ethylene uptake curves for Examples 8 and 12

OLIGOMERISATION OF OLEFINIC COMPOUNDS IN AN ALIPHATIC MEDIUM

TECHNICAL FIELD

This invention relates to the oligomerisation of olefinic compounds in an aliphatic liquid medium to produce oligomers.

BACKGROUND TO THE INVENTION

Conventional ethylene oligomerisation technologies produce a range of α-olefins following either a Schulz-Flory or Poisson product distribution. By definition, these mathematical distributions limit the mass % of the tetramer that can be formed and make a distribution of products. In this regard, it is known from prior art (U.S. Pat. No. 6,184,428) that a nickel catalyst comprising a chelating ligand, preferably 2-diphenyl phosphino benzoic acid (DPPBA), a nickel precursor, preferably $NiCl_2.6H_2O$, and a catalyst activator, preferably sodium tetraphenylborate, catalyse the oligomerisation of ethylene to yield a mixture of linear olefins containing 1-octene. The selectivity towards linear $C_8$-olefins is claimed to be 19%. Similarly the Shell Higher Olefins Process (SHOP process, U.S. Pat. Nos. 3,676,523 and 3,635,937) using a similar catalyst system is reported to typically yield 11 mass % 1-octene in its product mixture (Chem Systems PERP reports 90-1, 93-6 and 94/95S12).

Ziegler-type technologies based on trialkylaluminium catalysts, independently developed by Gulf Oil Chemicals Company (Chevron-Phillips, e.g. DE patent 1,443,927) and Ethyl Corporation (BP-Amoco, e.g. U.S. Pat. No. 3,906,053), are also commercially used to oligomerise ethylene to mixtures of olefins that reportedly contain 13-25 mass % 1-octene (Chem Systems PERP reports 90-1, 93-6, and 94/95S12).

The prior art also teaches that chromium-based catalysts containing heteroatomic ligands with both phosphorus and nitrogen heteroatoms selectively catalyse the trimerisation of ethylene to 1-hexene. Examples of such heteroatomic ligands for ethylene trimerisation include bis(2-diethylphosphinoethyl)amine (WO 03/053891) as well as (o-methoxyphenyl)$_2$ PN(methyl)P(o-methoxyphenyl)$_2$ (WO 02/04119). Both these catalyst systems and processes are very specific for the production of 1-hexene.

Processes wherein transition metals and heteroatomic ligands are combined to form catalysts for trimerisation, tetramerisation, oligomerisation and polymerisation of olefinic compounds have also been described in WO 03/053890, WO 03/053891, WO 04/056479, WO 04/056477, WO 04/056478, WO 04/056480 and South African provisional patent application number 2004/3805.

It has now been found that the oligomerisation of olefinic compounds by catalysts containing a transition metal and a ligand can be enhanced by carrying out the reaction in an aliphatic medium. In processes according to the present invention aliphatic solvents such as cyclohexane provided more active reaction systems compared to aromatic solvents, which can reduce catalyst consumption significantly. In at least some cases it has also been found that aliphatic solvents such as cyclohexane had the effect that the catalysts were less prone to deactivation at temperatures above 45° C. compared to reactions where aromatic solvents were used at the same temperatures. Certain activators such as MMAO had also shown improved activity and stability of the catalyst when used in aliphatic solvents such as cyclohexane. Increased pressures also enhanced the reaction.

BRIEF DESCRIPTION OF THE DRAWINGS

FIG. 1 is a graph showing cumulative ethylene uptake curves of Examples 8 and 12.

DISCLOSURE OF THE INVENTION

According to the present invention there is provided a process for producing an oligomeric product by the oligomerisation of at least one olefinic compound in the form of an olefin or a compound including an olefinic moiety by contacting the at least one olefinic compound with an oligomerisation catalyst in an aliphatic liquid medium at a reaction temperature of at least 50° C., wherein the catalyst comprises the combination of
i) a source of a transition metal; and
ii) a ligating compound of the formula

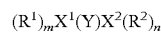

wherein:
$X^1$ and $X^2$ are independently selected from the group consisting of
N, P, As, Sb, Bi, O, S and Se;
Y is a linking group between $X^1$ and $X^2$;
m and n are independently 0, 1 or a larger integer; and
$R^1$ and $R^2$ are independently hydrogen, a hydrocarbyl group or a heterohydrocarbyl group, and $R^1$ being the same or different when m>1, and $R^2$ being the same or different when n>1.

In this specification an aliphatic liquid medium is at least one liquid aliphatic compound, that is an acyclic or a cyclic organic compound, including a saturated and/or an unsaturated carbon compound, but excluding an aromatic compound.

Oligomeric Product

The oligomeric product may be an olefin, or a compound including an olefinic moiety. Preferably the oligomeric product comprises an olefin, more preferably an olefin containing a single carbon-carbon double bond, and preferably it comprises an -olefin. The olefin product may comprise hexene, preferably 1-hexene, but more preferably it comprises octene, preferably 1-octene. The oligomeric product may comprise a mixture of hexene and octene, preferably a mixture of 1-hexene and 1-octene.

In one preferred embodiment of the invention the oligomerisation process is a selective process to produce a product containing more than 30% by mass of a single olefin product, preferably octene, and more preferably 1-octene. Preferably the product contains at least 35% of the olefin, preferably -olefin, preferably 1-octene, but it may be more than 40%, 50%, 60% or even 70% by mass.

The olefinic product may be branched, but preferably it is non-branched.

Oligomerisation

The oligomerisation process may comprise a trimerisation process, but preferably it comprises a tetramerisation process.

The process may be oligomerisation of two or more different olefinic units to produce an oligomer containing the reaction product of the two or more different olefinic units. Preferably however, the oligomerisation (preferably tetramerisation) comprises the oligomerisation of identical monomer olefinic units.

In one preferred embodiment of the invention the oligomerisation process is oligomerisation of a single -olefin to produce an oligomeric -olefin. Preferably it comprises the trimerisation and/or tetramerisation of ethylene, preferably to 1-hexene and/or 1-octene.

Olefinic Compound

The olefinic compound may comprise a single olefinic compound or a mixture of olefinic compounds. In one embodiment of the invention it may comprise a single olefin.

The olefin may include multiple carbon-carbon double bonds, but preferably it comprises a single carbon-carbon double bond. The olefin may comprise an -olefin with 2 to 30 carbon atoms, preferably 2 to 10 carbon atoms. The olefinic compound may be selected from the group consisting of ethylene, propene, 1-butene, 1-pentene, 1-hexene, 1-heptene, and 1-octene, 1-nonene, 1-decene, 3-methyl-1-butene, 3-methyl-1-pentene, 4-methyl-1-pentene, styrene, p-methyl styrene, 1-dodecene or combinations thereof. Preferably it comprises ethylene or propene, preferably ethylene. The ethylene may be used to produce hexene, preferably 1-hexene, and/or octene, preferably 1-octene.

Aliphatic Liquid Medium

The aliphatic liquid medium may comprise a at least one acyclic compound, but preferably it comprises at least one cyclic compound. The cyclic compound may include one or more hetero-atoms (that is atoms other that H and C), but preferably it is a cyclic hydrocarbon, including a cyclic hydrocarbon wherein a hydrogen atom bound to a ring atom of the cyclic hydrocarbon is substituted with a hydrocarbyl, including an alkyl. The cyclic hydrocarbon may include one or more unsaturated carbon to carbon bonds, but preferably it comprises a saturated cyclic hydrocarbon. The ring structure defined by the saturated cyclic hydrocarbon may consist of 3 to 12 carbon atoms, preferably 5 to 8 carbon atoms. In one embodiment of the invention the ring structure defined by the saturated cyclic hydrocarbon may consist of 6 carbon atoms.

In one preferred embodiment of the invention the aliphatic liquid medium may comprise cyclohexane. Last mentioned compound is especially suitable from a product separation/solvent recycle point of view in trimerisation of ethylene.

Alternatively, the aliphatic liquid medium may comprise a substituted cyclohexane wherein at least one (preferably only one) hydrogen atom of cyclohexane is substituted with a substitution moiety which is not H. The substitution moiety may comprise an organyl, preferably an alkyl. In one embodiment of the invention the aliphatic liquid medium may comprise methylcyclohexane. Last mentioned compound is especially suitable from a product separation/solvent recycle point of view in tetramerisation of ethylene.

It has been found that aliphatic liquid mediums such as cyclohexane provide higher reaction rates and catalyst stability (compared to aromatic liquid mediums) which can reduce catalyst usage. Aliphatic liquid mediums (e.g. cyclohexanes) are usually also more environmentally friendly than aromatic compounds.

The aliphatic liquid medium may comprise a saturated acyclic compound such as one or more isoparaffins or mixtures of isoparaffins and linear paraffins, or linear paraffins, preferably it comprises the products known in the trade as, Norpar, and Isopar, and more preferably it comprises Isopar C due to ease of separation of products from the solvent.

Preferably the liquid medium is an inert liquid medium.

In a preferred embodiment of the invention the aliphatic liquid medium is a solvent of the olefinic compound and/or the oligomerisation catalyst, preferably of both.

The aliphatic liquid medium may comprise a combination of one or more aliphatic compounds.

Reaction Temperature

The reaction temperature is at least 50° C., and preferably it is at least 60° C. The reaction temperature may be at least 80° C. and at least 85° C. and even as high as 100° C. or higher and even 125° C. The reaction temperature may be from 50 to 125° C.

It has been found that if oligomerisation reactions of this type were carried out in aromatic solvents the reaction temperature had to be limited to 45° C. or below as the higher temperatures result in faster deactivation of oligomerisation catalyst. It has now been found that if the reaction is carried out in an aliphatic solvent the catalyst is both less prone to deactivation at temperatures above 45° C. and catalyst activity is still acceptable, even higher in at least some cases, at the higher temperatures.

One disadvantage of having to limit the reaction temperature to a maximum of 45° C. is heat removal becomes very expensive, either requiring refrigeration or very large cooling water exchangers for removal of the oligomerisation reaction exotherm.

Most surprisingly it has also been found that in at least some cases at higher temperatures the oligomerisation process was more selective to high value oligomerisation products such as 1-hexene and 1-octene.

Pressure

The reaction is preferably carried out at a pressure above 1000 kPa, more preferably at least 4500 kPa, but even at least 5000 kPa, even at least 6000 kPa and even at least 8000 kPa or even higher.

Catalyst Activation

In a preferred embodiment of the invention the catalyst also includes one or more activators. Such an activator may be a compound that generates an active catalyst when the activator is combined with the source of transition metal and the ligating compound.

Suitable activators include aluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

Suitable aluminium compounds include compounds of the formula $Al(R^9)_3$ ($R^9$ being the same or different), where each $R^9$ is independently a $C_1$-$C_{12}$ alkyl, an oxygen containing moiety or a halide, aluminoxanes, and compounds such as $LiAlH_4$ and the like. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Examples of suitable aluminium compounds in the form of organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), isobutylaluminoxane (iBuAO), modified alkylaluminoxanes such as modified methylaluminoxane (MMAO). and mixture thereof.

Examples of suitable organoboron compounds are boroxines, $NaBH_4$, triethylborane, tris(pentafluorophenyl)borane, trityl tetrakis(pentafluorophenyl) borate, dimethylanilinium tetrakis(pentafluorophenyl)borate, tributyl borate and the like.

The activator may also be or contain a compound that acts as a reducing or oxidising agent, such as sodium or zinc metal and the like, or hydrogen or oxygen and the like.

The activator may be selected from alkylaluminoxanes such as methylaluminoxane (MAO), high stabiliIy methylaluminoxane (MAO HS), ethylaluminoxane (EAO), isobutylaluminium (iBuAO) as well as modified alkylaluminoxanes such as modified methylaluminoxane (MMAO). MMAO is described later in this specification.

The transition metal source and the aluminoxane may be combined in proportions to provide Al/transition metal molar ratios from about 1:1 to 10 000:1, preferably from about 1:1 to 1000:1, and more preferably from 1:1 to 500:1.

The process may include the step of adding to the catalyst system a trialkylaluminium compound in amounts of between 0.01 to 1000 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete hydrolysis with water. Any quantity of a trialkylaluminium compound quoted in this disclosure is additional to alkylaluminium compounds contained within the aluminoxanes.

It has been found that modified methylaluminoxane (MMAO) is especially suitable as an activator which may result in improved activity of the catalyst including less deactivation of the catalyst.

MMAO is methyl aluminoxane wherein one or more, but not all methyl groups have been replaced by one or more non-methyl moieties. Preferably the non-methyl moiety is an organyl, preferably a hydrocarbyl or a heterohydrocarbyl. Preferably it is an alkyl, preferably isobutyl or n-octyl. It may be a product supplied by Akzo Nobel.

Source of Transition Metal

Preferably the source of transition metal is a source of a Group IV to VI transition metal. Preferably it is a source of Cr, Ti, V, Ta or Zr. Preferably it is a source of either Cr, Ta or Ti. Most preferably it is a source of Cr.

The source of the Group IV to VI transition metal may be an inorganic salt, an organic salt, a coordination compound or an organometallic complex.

Preferably the source of transition metal is a source of chromium and preferably it is selected from the group consisting of chromium trichloride tris-tetrahydrofuran complex; (benzene)tricarbonyl chromium; chromium (III) octanoate; chromium hexacarbonyl; chromium (III) acetylacetonate, and chromium (III) 2-ethylhexanoate. Preferably it is selected from chromium (III) acetylacetonate, chromium (III) 2-ethylhexanoate, and chromium trichloride tris-tetrahydrofuran complex.

Ligating Compound $X^1$ and/or $X^2$ may be a potential electron donor for coordination with the transition metal.

An electron donor is defined as an entity that donates electrons used in chemical, including dative covalent, bond formation.

$X^1$ and/or $X^2$ may be independently oxidised by S, Se, N or O.

$X^1$ and/or $X^2$ may be independently phosphorus or phosphorus oxidised by S or Se or N or O. Preferably $X^1$ and $X^2$ are the same, and preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m an n are not 0.

Preferably the ligating compound is of the formula

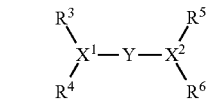

wherein Y is as defined above; $X^1$ and $X^2$ are independently selected from the group consisting of N, P, As, Sb and Bi; and $R^3$ to $R^6$ are each independently a hydrocarbyl group or a heterohydrocarbyl group.

Preferably $X^1$ and $X^2$ are independently selected from the group consisting of P and N. Preferably $X^1$ and $X^2$ are the same. Preferably both $X^1$ and $X^2$ are P.

One or more of $R^3$ to $R^6$ may be a substituted hydrocarbyl group or a substituted heterohydrocarbyl group, that is at least one substituent is bound to the hydrocarbyl group or the heterohydrocarbyl group. In this specification a substituent is a moiety (excluding H) which is bound to a linear structure or a cyclic structure bound to $X^1$ or $X^2$, but does not form part of the linear or cyclic structure.

The linear or cyclic structure may be selected from the group consisting of a linear hydrocarbyl, a cyclic hydrocarbyl and a cyclic heterohydrocarbyl group. Linear hydrocarbyl may include ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl. According to the above definition and for the purpose of clarity, benzyl is considered as a methyl linear structure with a phenyl substituent and tolyl is considered to be a phenyl cyclic structure with a methyl substituent.

It will also be appreciated that a group such as $H_2ClC-$ is, in terms of this specification considered as a heterohydrocarbyl group and not a substituted hydrocarbyl group.

$R^3$ to $R^6$ may also be selected from a group of metallocenes such as a ferroceneyl, zirconoceneyl and titanoceneyl group.

Preferably none of $R^3$ to $R^6$ are aromatic with a ring atom of the aromatic ring structure bound to either $X^1$ and $X^2$ and with a polar substituent as a non-ring atom bound to a ring atom of the aromatic ring structure adjacent to the ring atom bound to $X^1$ or $X^2$.

In this specification a polar substituent is a substituent with a permanent electric or induced dipole moment.

Preferably, if two or more of $R^3$ to $R^6$ are aromatic with a ring atom of the aromatic ring structure bound to $X^1$ or $X^2$, not more than two of said aromatic $R^3$ to $R^6$ have a substituent as a non-ring atom bound to a ring atom of the aromatic ring structure adjacent to the ring atom bound to $X^1$ or $X^2$.

In one embodiment of the invention $R^3$ to $R^6$ are the same or different and each is a hydrocarbyl group, or a heterohydrocarbyl group which contains no substitutent or contains a non-polar substituent. Preferably each of $R^3$ to $R^6$ does not have any polar substituent. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a non-polar substituent other than H as a non-ring atom bound to a ring atom of the aromatic ring structure adjacent to the ring atom bound to $X^1$ or $X^2$. Preferably none of the aromatic $R^3$ to $R^6$ have a non-polar substituent as a non-ring atom bound to a ring atom of the aromatic ring structure adjacent to the ring atom bound to $X^1$ or $X^2$. Preferably all of aromatic $R^3$ to $R^6$ are non-substituted aromatic compounds. $R^3$ to $R^6$ may be independently selected from the group consisting of a non-aromatic compound; an aromatic compound; and a heteroaromatic compound. Preferably each of $R^3$ to $R^6$ is an aromatic or heteroaromatic compound, more preferably an aromatic compound (including a substituted aromatic compound). The aromatic compound (or substituted aromatic compound) may comprise phenyl or a substituted phenyl.

In this specification a non-polar substituent is a substituent without a permanent electric or induced dipole moment.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexenyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may be independently linked to one or more of each other, or to Y to form a cyclic structure.

$R^3$ and $R^4$ may be the same and $R^5$ and $R^6$ may be the same. $R^3$ to $R^6$ may all be the same.

In another embodiment of the invention $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may be independently selected from the group consisting of a substituted non-aromatic compound; a substituted aromatic compound; and a substituted heteroaromatic compound. Preferably each of $R^3$ to $R^6$ is a substituted aromatic or a substituted heteroaromatic compound, more preferably a substituted aromatic compound. The substituted aromatic compound may comprise a substituted phenyl. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a substituent as a non-ring atom bound to a ring atom of the aromatic ring structure adjacent to the ring atom bound to $X^1$ or $X^2$.

Any polar substituent on one or more of $R^3$, $R^4$, $R^5$ and $R^6$ may be electron donating.

Suitable polar substituents may be a methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro halides or the like.

Y may be selected from the group consisting of an organic linking group such as a hydrocarbyl, substituted hydrocarbyl, heterohydrocarbyl and a substituted heterohydrocarbyl; an inorganic linking group such as a single atom link (that is $X^1$ and $X^2$ are bound to the same atom); methylene; dimethylmethylene; 1,2-ethane; 1,2-ethene; 1,1-cyclopropane; 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol and 1,2-dialkylhydrazine; —B($R^7$)—, —Si($R^7$)$_2$—, —P($R^7$)— and —N($R^7$)— where $R^7$ is hydrogen, a hydrocarbyl or heterocarbyl or halogen. Preferably, Y may be —N($R^7$)— and $R^7$ may be selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^7$ may be a hydrocarbyl or a substituted hydrocarbyl group. $R^7$ may be methyl, ethyl, propyl, isopropyl, cyclopropyl, allyl, butyl, tertiary-butyl, sec-butyl, cyclobutyl, pentyl, isopentyl, neopentyl, cyclopentyl, cyclohexyl, cycloheptyl, cyclo-octyl, decyl, cyclodecyl, 1,5-dimethylheptyl, 2-naphthylethyl, 1-naphthylmethyl, adamantylmethyl, adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethylcyclohexyl, exo-2-norbornanyl, isopinocamphenyl, dimethylamino, phthalimido, pyrrolyl, trimethylsilyl, dimethyl-tertiary-butylsilyl, 3-trimethoxylsilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, 1,2,3,4-tetrahydronaphthyl, or a 2-octyl group.

Y may exclude $(CH_2)_xZ(CH_2)_y$, where Z is —P($R^8$)—, —N($R^8$)—, —As($R^8$)—, —Sb($R^8$)— or —S— and x and y are individually 1-15 and wherein $R^8$ is hydrogen or a halogen or a nitro group or a hydrocarbyl or a substituted hydrocarbyl group.

Y may include a first atom bound to $X^1$ and a different atom bound to $X^2$.

Preferably Y includes or is a single atom bound to both $X^1$ and $X^2$.

Preferably the ligating compound is of the formula

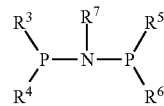

with $R^3$ to $R^7$ as defined above.

Preferably each of $R^3$ to $R^6$ is an alkyl (preferably methyl, ethyl or isopropyl) or aromatic (preferably phenyl or substituted phenyl).

Preferably the ligating compound is a bidentate ligand.

Non limiting examples of the ligating compound are (phenyl)$_2$PN(methyl)P(phenyl)$_2$; (phenyl)$_2$PN(ethyl)P(phenyl)$_2$; (phenyl)$_2$PN(propyl)P(phenyl)$_2$; (phenyl)$_2$PN(butyl)P(phenyl)$_2$; (phenyl)$_2$PN(pentyl)P(phenyl)$_2$; (phenyl)$_2$PN(hexyl)P(phenyl)$_2$; (phenyl)$_2$PN(heptyl)P(phenyl)$_2$; (phenyl)$_2$PN(octyl)P(phenyl)$_2$; (phenyl)$_2$PN(nonyl)P(phenyl)$_2$; (phenyl)$_2$PN(decyl)P(phenyl)$_2$, (phenyl)$_2$PN(cyclopropyl)P(phenyl)$_2$; (phenyl)$_2$PN(cyclobutyl)P(phenyl)$_2$; (phenyl)$_2$PN(cyclopentyl)P(phenyl)$_2$; (phenyl)$_2$PN(cyclohexyl)P(phenyl)$_2$; (phenyl)$_2$PN(cycloheptyl)P(phenyl)$_2$; (phenyl)$_2$PN(cyclooctyl)P(phenyl)$_2$; (phenyl)$_2$PN(cyclodecyl)P(phenyl)$_2$; (phenyl)$_2$PN(cyclododecyl)P(phenyl)$_2$; (phenyl)$_2$PN(isopropyl)P (phenyl)₂; (phenyl)₂PN(isobutyl)P(phenyl)₂; (phenyl)₂PN(secbutyl)P(phenyl)₂; (phenyl)₂PN(tertiarybutyl)P(phenyl)₂; (phenyl)₂PN(neopentyl)P(phenyl)₂; (phenyl)₂PN(1,2-dimethyl-propyl)P(phenyl)₂; (phenyl)₂PN(allyl)P(phenyl)₂; (phenyl)₂PN(methylheptyl)P(phenyl)₂; (phenyl)₂PN(1,5-dimethyl-heptyl)P(phenyl)₂; (phenyl)₂PN(2-ethylhexyl)P(phenyl)₂; (phenyl)₂PN(adamantyl)P(phenyl)₂; (phenyl)₂PN(adamantylmethyl)P(phenyl)₂; (phenyl)₂PN(3-trimethoxysilane-propyl)P(phenyl)₂; (phenyl)₂PN(indanyl)P(phenyl)₂; (phenyl)₂PN(cyclohexylethyl)P(phenyl)₂; (phenyl)₂PN(2-methylcyclohexyl)P(phenyl)₂; (phenyl)₂PN(cyclohexanemethyl)P(phenyl)₂; (phenyl)₂PN(benzyl)P(phenyl)₂; (phenyl)₂PN(phenyl)P(phenyl)₂; (phenyl)₂PN((4-methoxy)-phenyl)P(phenyl)₂; (phenyl)₂PN((3-methoxy)-phenyl)P(phenyl)₂; (phenyl)₂PN((2-methoxy)phenyl)P(phenyl)₂; (phenyl)₂PN((4-t-butyl)-phenyl)P (phenyl)₂; (phenyl)₂PN((4-nitro)-phenyl)P(phenyl)₂; (phenyl)₂PN(1-naphthyl)P(phenyl)₂; (phenyl)₂PN(2-naphthyl)P(phenyl)₂; (phenyl)₂PN(4-pyridyl)P(phenyl)₂(phenyl)₂PN(3-(N-morpholine)-propyl)P(phenyl)₂; (phenyl)₂PN(2-naphtyl-ethyl)P(phenyl)₂; (phenyl)₂PN(1-naphtylmethyl)P(phenyl)₂; (phenyl)₂PN(diphenylmethyl)P(phenyl)₂; (phenyl)₂PN(1,2-diphenyl-ethyl)P(phenyl)₂; (phenyl)₂PN(phenylethyl)P(phenyl)₂; (phenyl)₂PN((2-methyl)phenyl)P(phenyl)₂; (phenyl)₂PN((3-methyl)phenyl)P(phenyl)₂; (phenyl)₂PN((4-methyl)phenyl)P(phenyl)₂; (phenyl)₂PN((2,6-dimethyl)phenyl)P(phenyl)₂; (phenyl)₂PN((2-ethyl)-phenyl)P(phenyl)₂; (phenyl)₂PN(1,2,3,4-Tetrahydronaphthyl)P(phenyl)₂; (phenyl)₂PN((2-methyl)cyclohexyl)P(phenyl)₂; (phenyl)₂PN((3-methyl)cyclohexyl)P(phenyl)₂; (phenyl)₂PN((4-methyl)cyclohexyl)P(phenyl)₂, (phenyl)₂PN((2-ethyl)cyclohexyl)P(phenyl)₂; (phenyl)₂PN((2-isopropyl)cyclohexyl)P(phenyl)₂; (phenyl)₂PN((2,6-dimethyl)cyclohexyl)P(phenyl)₂; (phenyl)₂PN(exo-2-norbornanyl)P(phenyl)₂; (phenyl)₂PN(isopinocampheyl)P(phenyl)₂; (phenyl)₂PN(dimethylamino)P(phenyl)₂; (phenyl)₂PN(phthalimido)P(phenyl)₂; (phenyl)₂ PN(pyrrolyl)P(phenyl)₂; (phenyl)₂PN(trimethylsiyl)P(phenyl)₂; (phenyl)₂PN(dimethyltertiarybutylsilyl)P(phenyl)₂; [(phenyl)₂P₂]N(1,1'-bis(cyclohexyl)-4,4'-methylene))N[P(phenyl)₂]₂; ([(phenyl)₂ P]₂N(1,6-hexylene-)N[P(phenyl)₂]₂; (2,2',2"-triethylamino)[N[P(phenyl)₂]₂]₃; (4-biphenyl)PN(methyl)P(4-biphenyl)₂; (2-naphthyl)₂PN(methyl)P(2-naphthyl)₂; (4-methylphenyl)₂PN(methyl)P(4-methylphenyl)₂; (3-methylphenyl)₂PN(methyl)P(3-methylphenyl)₂; (2-naphthyl)₂PN(methyl)P(phenyl)₂; (2-naphthyl)(phenyl)PN(methyl)P(2-naphthyl)(phenyl); (2-naphthyl)₂PN(methyl)P(2-naphthyl)(phenyl); (2-naphthyl)(phenyl)PN(methyl)P(phenyl)₂; (2-methylphenyl)₂PN(methyl)P(2-methyl phenyl)₂; (2-ethylphenyl)₂PN(methyl)P(2-ethylphenyl)₂; (2-isopropylphenyl)₂PN(methyl)P(2-isopropylphenyl)₂; (2-methylphenyl)₂PN(ethyl)P(2-methylphenyl)₂; (2-methylphenyl)₂PN(methyl)P(2-methylphenyl)(phenyl); (2-methylphenyl)(phenyl)PN(isopropyl)P(2-methylphenyl)(phenyl); (2-methylphenyl)₂ PN(methyl)P(phenyl)₂; (2-methylphenyl)(phenyl)PN(isopropyl)P(phenyl)₂; (ethyl)₂PN(methyl)P(ethyl)₂; (ethyl)₂ PN(isopropyl)P(ethyl)₂; (ethyl)₂PN(tertiarybutyl)P(ethyl)₂; (methyl)₂PN(isopropyl)P(methyl)₂; (isopropyl)₂PN(methyl)P(isopropyl)₂, (ethyl)₂PN(isopropyl)P(ethyl)(phenyl); (ethyl)(phenyl)PN(isopropyl)P(ethyl)(phenyl); (ethyl)₂PN(isopropyl)P(phenyl)₂; (ethyl)(phenyl)PN(isopropyl)P(phenyl)₂; (2-thipheneyl)₂PN(isopropyl)P(2-thipheneyl)₂; (diphenylphosphonite)N(isopropyl)(diphenylphosphonite); (dibenzothiaphosphonine)N(isopropyl)(dibenzothiaphosphonine); (dibenzooxaphosphonine)N(isopropyl)(dibenzooxaphosphonine); (phenyl)₂PN(methyl)N(methyl)P(phenyl)₂; (phenyl)₂PN(ethyl)N(ethyl)P(phenyl)₂; (phenyl)₂PN(phenyl)N(phenyl)P(phenyl)₂; (phenyl)₂PN(isopropyl)N(isopropyl)P(phenyl)₂; (phenyl)₂PN(isopropyl)N(methyl)P(phenyl)₂; (phenyl)₂PN(isopropyl)N(methyl)P(phenyl)₂; (4-methylphenyl)₂P—N(CH₃)N(CH₃)—P(4-methyl phenyl)₂; (3-methylphenyl)₂P—N(CH₃)N(CH₃)—P(3-methylphenyl)₂; (2-methylphenyl)₂P—N(CH₃)N(CH₃)—P(2-methylphenyl)₂; (2-ethylphenyl)₂P—N(CH₃)N(CH₃)—P(2-ethylphenyl)₂; (2-isopropylphenyl)₂P—N(CH₃)N(CH₃)—P(2-isopropylphenyl)₂; (2-methylphenyl)₂P—N(CH₃)N(CH₃)—P(2-methylphenyl)(phenyl); (2-methlylphenyl)₂P—N(CH₃)N(CH₃)—P(phenyl)₂; (ethyl)₂P—N(CH₃)N(CH₃)—P(ethyl)₂; (methyl)₂P—N(CH₃)N(CH₃)—P(methyl)₂; (isopropyl)₂P—N(CH₃)N(CH₃)—P(isopropyl)₂; (ethyl)₂P—N(CH₃)N(CH₃)—P(ethyl)(phenyl); (ethyl)(phenyl)P—N(CH₃)N(CH₃)—P(ethyl)(phenyl); (ethyl)₂P—N(CH₃)N(CH₃)—P(phenyl)₂; (ethyl)(phenyl)P—N(CH₃)N(CH₃)—P(phenyl)₂; (2-thipheneyl)₂P—N(CH₃)N(CH₃)—P(2-thipheneyl)₂, (2-naphthyl)₂P—N(CH₃)N(CH₃)—P(2-naphthyl)₂; (4-biphenyl)₂P—N(CH₃)N(CH₃)—P(4-biphenyl)₂; (phenyl)₂P-1,8-naphthyl-P(phenyl)₂; (phenyl)₂P-9,10-phenanthrene-P(phenyl)₂; (phenyl)₂P-4,5-phenanthrene-P(phenyl)₂; (phenyl)₂P—C(CH₃)₂—P(phenyl)₂; (phenyl)₂P—C(CH₂)₂—P(phenyl)₂; (phenyl)₂P-1,2-benzene-P(phenyl)₂; (4-methylphenyl)₂P-1,2-benzene-P(4-methylphenyl)₂; (3-methylphenyl)₂P-1,2-benzene-P(3-methylphenyl)₂; (2-methylphenyl)₂P-1,2-benzene-P(2-methylphenyl)₂; (2-ethylphenyl)₂P-1,2-benzene-P(2-ethylphenyl)₂; (2-isopropylphenyl)₂P-1,2-benzene-P(2-isopropylphenyl)₂; (2-methylphenyl)₂P-1,2-benzene-P(2-methylphenyl)(phenyl); (2-methlylphenyl)₂P-1,2-benzene-P(phenyl)₂; (ethyl)₂P-1,2-benzene-P(ethyl)₂; (methyl)₂P-1,2-benzene-P(methyl)₂; (isopropyl)₂P-1,2-benzene-P(isopropyl)₂; (ethyl)₂P-1,2-benzene-P(ethyl)(phenyl); (ethyl)(phenyl)P-1,2-benzene-P(ethyl)(phenyl); (ethyl)₂P-1,2-benzene-P(ethyl)₂; (ethyl)(phenyl)P-1,2-benzene-P(phenyl)₂; (2-thipheneyl)₂P-1,2-benzene-P(2-thipheneyl)₂; (2-naphthyl)₂P-1,2-benzene-P(2-naphthyl)₂; (4-biphenyl)₂P-1,2-benzene-P(4-biphenyl)₂; (phenyl)₂P—CH₂CH₂—P(phenyl)₂; (4-methylphenyl)₂P—CH₂CH₂—P(4-methylphenyl)₂; (3-methylphenyl)₂P—CH₂CH₂—P(3-methyl phenyl)₂; (4-methylphenyl)₂P—CH₂CH₂—P(4-methylphenyl)(phenyl); (4-methylphenyl)(phenyl)P—CH₂CH₂—P(4-methylphenyl)(phenyl); (4-methylphenyl)₂P—CH₂CH₂—P(phenyl)₂; (4-methylphenyl)(phenyl)P—CH₂CH₂—P(phenyl)₂; (2-methylphenyl)₂P—CH₂CH₂—P(2-methylphenyl)₂; (2-ethylphenyl)₂P—CH₂CH₂—P(2-ethylphenyl)₂; (2-isopropylphenyl)₂P—CH₂CH₂—P(2-isopropylphenyl)₂; (2-methylphenyl)₂P—CH₂CH₂—P(2-methylphenyl)(phenyl); (2-methlylphenyl)₂P—CH₂CH₂—P(phenyl)₂; (ethyl)₂P—CH₂CH₂—P(ethyl)₂; (methyl)₂P—CH₂CH₂—P(methyl)₂; (isopropyl)₂P—CH₂CH₂—P(isopropyl)₂; (ethyl)₂P—CH₂CH₂—P(ethyl)(phenyl); (ethyl)(phenyl)P—CH₂CH₂—P(ethyl)(phenyl); (ethyl)₂P—CH₂CH₂—P(phenyl)₂; (ethyl)(phenyl)P—CH₂CH₂—P(phenyl)₂; (2-thipheneyl)₂P—CH₂CH₂—P(2-thipheneyl)₂; (phenyl)₂PB(phenyl)P(Phenyl)₂; (phenyl)₂PP(phenyl)P(phenyl)₂; (phenyl)₂PSi(methyl)₂P(phenyl)₂; (phenyl)₂AsN(isopropyl)As(phenyl)₂; (phenyl)SN(isopropyl)S(phenyl); (phenyl)₂PN(isopropyl)S(phenyl); (phenyl)₂PN(isopropyl)As(phenyl)₂; (phenyl)₂PN(isopropyl)P(═O)(phenyl)₂; (phenyl)₂P(═O)N(isopropyl)P(═O)(phenyl)₂; (phenyl)₂PN(isopropyl)P(═S)(phenyl)₂; (phenyl)₂P(═S)N(isopropyl)P(═S)(phenyl)₂; (phenyl)₂P(═O)N(isopropyl)P(═S)(phenyl)₂; (4-trifluoromethylphenyl)₂PN(isopropyl)P(4-trifluoromethylphenyl)₂; (4-chlorophenyl)₂PN(isopropyl)P(4-chlorophenyl)₂; (4-methoxyphenyl)₂PN(methyl)P(4- methoxyphenyl)₂; (4-methoxyphenyl)₂PN(isopropyl)P(4-methoxyphenyl)₂; (3-methoxyphenyl)₂PN(methyl)P(3-methoxyphenyl)₂; (4-methoxyphenyl)₂PN(isopropyl)P(4-methoxyphenyl)(phenyl); (4-methoxyphenyl)(phenyl)PN(isopropyl)P(4-methoxyphenyl)(phenyl); (4-methoxyphenyl)₂PN(isopropyl)P(phenyl)₂; (4-methoxyphenyl)(phenyl)PN(isopropyl)P(phenyl)₂; (4-methoxyphenyl)₂P—N(CH₃)N(CH₃)—P(4-methoxyphenyl)₂; (3-methoxyphenyl)₂P—N(CH₃)N(CH₃)—P(3-methoxyphenyl)₂; (4-methoxyphenyl)₂ P—N(CH₃)N(CH₃)—P(4-methoxyphenyl)(phenyl); (4-methoxyphenyl)(phenyl)P—N(CH₃)N(CH₃)—P(4-methoxyphenyl)(phenyl); (4-methoxyphenyl)₂P—N(CH₃)N(CH₃)—P(phenyl)₂; (4-methoxyphenyl)(phenyl)P—N(CH₃)N(CH₃)—P(phenyl)₂; (4-methoxyphenyl)₂P-1,2-benzene-P(4-methoxyphenyl)₂; (3-methoxyphenyl)₂P-1,2-benzene-P(3-methoxyphenyl)₂; (4-methoxyphenyl)₂P-1,2-benzene-P(4-methoxyphenyl)(phenyl); (4-methoxyphenyl)(phenyl)P-1,2-benzene-P(4-methoxyphenyl)(phenyl); (4-methoxyphenyl)₂P-1,2-benzene-P(phenyl)₂; (4-methoxyphenyl)(phenyl)P-1,2-benzene-P(phenyl)₂; (3-methoxyphenyl)₂P(CH₂CH₂)P(3-methoxyphenyl)₂; (3-methoxyphenyl)₂P(CH₂CH₂)P(3-methoxyphenyl)(phenyl); (3-methoxyphenyl)(phenyl)P(CH₂CH₂CH₂)P(3-methoxyphenyl)(phenyl); (3-methoxyphenyl)(phenyl)P(CH₂CH₂)P(3-methoxyphenyl)(phenyl); (3-methoxyphenyl)(phenyl)P(CH₂)P(3-methoxyphenyl)(phenyl); (3-methloxyphenyl)₂P(CH₂CH₂)P(phenyl)₂; (3-methoxyphenyl)(phenyl)P(CH₂CH₂)P (phenyl)₂; (4-methoxyphenyl)₂P(CH₂CH₂)P(4-methoxyphenyl)₂; (4-methoxyphenyl)₂P(CH₂CH₂)P(4-methoxyphenyl)(phenyl); (4-methoxyphenyl)(phenyl)P(CH₂CH₂CH₂)P(4-methoxyphenyl)(phenyl); (4-methoxyphenyl)(phenyl)P(CH₂CH₂)P(4-methoxyphenyl)(phenyl); (4-methoxyphenyl)(phenyl)P(CH₂)P(4-methoxyphenyl)(phenyl); (4-methloxyphenyl)₂P(CH₂CH₂)P (phenyl)₂; (4-methoxyphenyl)(phenyl)P(CH₂CH₂)P (phenyl)₂; (2-methoxyphenyl)₂PN(methyl)P(2-methoxyphenyl)₂; (2-methoxyphenyl)₂PN(ethyl)P(2-methoxyphenyl)₂; (2-methoxyphenyl)₂PN(phenyl)P(2-methoxyphenyl)₂; (2-methoxyphenyl)₂PN(methyl)N(methyl)P(2-methoxyphenyl)₂; (2-methoxyphenyl)₂P(CH₂)P(2-methoxyphenyl)₂; (2-methoxyphenyl)₂P(CH₂CH₂)P(2-methoxyphenyl)₂; tri (2-methoxyphenyl)phosphane; tri(2-methoxymethoxyphenyl)phosphane; (2-methoxyphenyl)₂PN(isopropyl)P(2-methoxyphenyl)(phenyl); (2-methoxyphenyl)(phenyl)PN (isopropyl)P(2-methoxyphenyl)(phenyl); (2-methloxyphenyl)₂PN(isopropyl)P(phenyl)₂; (2-methoxyphenyl)(phenyl)PN(isopropyl)P(phenyl)₂; (2-methoxyphenyl)₂PN(methyl)P(2-methoxyphenyl)(phenyl); (2-methoxyphenyl)(phenyl)PN(methyl)P(2-methoxyphenyl)(phenyl); (2-methloxyphenyl)₂PN(methyl)P(phenyl)₂; (2-methoxyphenyl)(phenyl)PN(methyl)P(phenyl)₂; (2-ethoxyphenyl)₂PN(methyl)P(2-ethoxyphenyl)₂; (2-isopropoxyphenyl)₂PN(methyl)P(2-isopropoxyphenyl)₂; (2-hydroxyphenyl)₂PN(methyl)P(2-hydroxyphenyl)₂; (2-nitrophenyl)₂PN(methyl)P(2-nitrophenyl)₂; (2-(dimethylamino)phenyl)₂PN(methyl)P(2-(dimethylamino)phenyl)₂; (2,3-dimethoxyphenyl)₂PN(methyl)P(2,3-dimethoxyphenyl)₂; (2,4-dimethoxyphenyl)₂PN(methyl)P(2,4-dimethoxyphenyl)₂; (2,6-dimethoxyphenyl)₂PN(methyl)P(2,6-dimethoxyphenyl)₂; (2,4,6-trimethoxyphenyl)₂PN(methyl)P(2,4,6-tri-methoxyphenyl)₂; (2-methoxyphenyl)(2-methylphenyl)PN(methyl)P(2-methylphenyl)₂; (2-methoxymethoxyphenyl)₂PN(methyl)P(2-methoxymethoxyphenyl)₂; (2-methoxyphenyl)₂PN(methyl) P(2-methoxyphenyl)(phenyl); (2-methoxyphenyl)(phenyl) PN(methyl)P(2-methoxyphenyl)(phenyl); (2-methloxyphenyl)₂PN (methyl)P(phenyl)₂; (2-methoxyphenyl)(phenyl)PN(methyl)P(phenyl)₂, (2-methoxyphenyl)₂P—N(CH₃)N(CH₃)—P(2-methoxyphenyl)₂; (2-methoxyphenyl)₂P-1,2-benzene-P(2-methoxyphenyl)₂; (2-methoxyphenyl)₂P(CH₂CH₂)P(2-methoxyphenyl)₂; (2-methoxyphenyl)₂P(CH₂CH₂)P(2-methoxyphenyl)(phenyl); (2-methoxyphenyl)(phenyl)P(CH₂CH₂CH₂)P(2-methoxyphenyl)(phenyl); (2-methoxyphenyl)(phenyl)P(CH₂CH₂)P(2-methoxyphenyl)(phenyl); (2-methoxyphenyl)(phenyl)P(CH₂)P(2-methoxyphenyl)(phenyl); (2-methloxyphenyl)₂P(CH₂CH₂)P(phenyl)₂; (2-methoxyphenyl)(phenyl)P(CH₂CH₂)P(phenyl)₂; (2-ethoxyphenyl)₂P(CH₂CH₂)P(2-ethoxyphenyl)₂; (2-ethoxyphenyl)₂P(CH₂CH₂)P(2-ethoxyphenyl)(phenyl); (2-ethoxyphenyl)(phenyl)P(CH₂CH₂)P(2-ethoxyphenyl)(phenyl); (2-ethoxyphenyl)(phenyl)P(CH₂CH₂)P(2-ethoxyphenyl)(phenyl); (2-ethoxyphenyl)(phenyl)P(CH₂)P(2-ethoxyphenyl)(phenyl); (2-ethoxyphenyl)₂P(CH₂CH₂)P(phenyl)₂; (2-ethoxyphenyl)(phenyl)P(CH₂CH₂)P(phenyl)₂; (2-isopropoxyphenyl)₂P(CH₂CH₂)P(2-isopropoxyphenyl)₂; (2-isopropoxyphenyl)₂P(CH₂CH₂)P(2-isopropoxyphenyl)(phenyl); (2-isopropoxyphenyl)(phenyl)P(CH₂CH₂CH₂)P(2-isopropoxyphenyl)(phenyl); (2-isopropoxyphenyl)(phenyl)P(CH₂CH₂)P(2-isopropoxyphenyl)(phenyl); (2-isopropoxyphenyl)(phenyl)P(CH₂)P(2-isopropoxyphenyl)(phenyl); (2-isopropoxyphenyl)₂P(CH₂CH₂)P(phenyl)₂; (2-isopropoxyphenyl)(phenyl)P(CH₂CH₂)P(phenyl)₂; (phenyl)₂PCH₂CH₂NHCH₂CH₂P(phenyl)₂; (ethyl)₂PCH₂CH₂NHCH₂CH₂P(ethyl)₂; (phenyl)₂PCH₂CH₂NHCH₂CH₂P(ethyl)₂; (phenyl)(ethyl) PCH₂CH₂NHCH₂CH₂P(phenyl)₂; (phenyl) SCH₂CH₂NHCH₂CH₂S(phenyl); (ethyl)₂PCH₂CH₂NHCH₂CH₂P(ethyl)₂; (decyl)₂PCH₂CH₂NHCH₂CH₂P(decyl)₂; (phenyl)₂PCH₂CH₂NHCH₂CH₂S(ethyl); (phenyl)₂PCH₂CH₂P(phenyl)CH₂CH₂P(phenyl)₂ and (phenyl)₂PCH₂CH₂CH₂NHCH₂CH₂P(phenyl)₂.

The ligating compound may include a polymeric moiety to render the reaction product of the source of transition metal and the said ligating compound to be soluble at higher temperatures and insoluble at lower temperatures e.g. 25° C. This approach may enable the recovery of the complex from the reaction mixture for reuse and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P (phenyl)₂)₂)-benzene, 1,4-di-(N(P(phenyl)₂)₂)-benzene, N(CH₂CH₂N(P(phenyl)₂)₂)₃, 1,4-di-(P(phenyl)N(methyl)P (phenyl)₂)-benzene, 1,2-di-(N(P(p-methoxyphenyl)₂)₂)-benzene, 1,4-di-(N(P(p-methoxyphenyl)₂)₂)-benzene, N(CH₂CH₂N(P(p-methoxyphenyl)₂)₂)₃ and 1,4-di-(P(p-methoxyphenyl)N(methyl)P(p-methoxyphenyl)₂)-benzene.

The ligating compounds may be prepared using procedures known to one skilled in the art and procedures forming part of the state of the art.

The oligomerisation catalyst may be prepared in situ, that is in the reaction mixture in which the oligomerisation reaction is to take place. Reaction mixture will be understood to include a reaction medium, reactants (olefinic compounds), reaction products and catalyst components. Typically the oligomerisation catalyst will be prepared in situ. However it is foreseen that the catalyst may be pre-formed or partly pre-formed.

The source of transition metal and ligating compound may be combined (in situ or ex situ) to provide any suitable molar ratio, preferably a transition metal to ligand compound molar ratio, from about 0.01:100 to 10 000:1, preferably from about 0.1:1 to 10:1.

The process may also include combining one or more different sources of transition metal with one or more different ligating compounds.

The oligomerisation catalyst or its individual components, in accordance with the invention, may also be immobilised by supporting it on a support material, for example, silica, alumina, $MgCl_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

Process

The olefinic compound or mixture thereof to be oligomerised according to this invention can be introduced into the process in a continuous or batch fashion.

Preferably, the reaction conditions of the process are chosen such to produce oligomers (especially trimers and tetramers) in high yield by selectively converting an ethylenic feedstock such as ethylene.

The process may include a process for the oligomerisation (especially tri- and/or tetramerisation) of ethylene or propylene or a mixture of olefins to yield an oligomerised product selectively.

The individual components constituting the oligomerisation catalyst described herein may be combined simultaneously or sequentially in any order to give an active oligomerisation catalyst. The presence of an olefinic compound during the mixing of the catalyst components generally provides a protective effect which may result in improved catalyst performance.

The reaction products derived from the oligomerisation reaction as described herein, may be prepared using the disclosed catalyst by a homogeneous liquid phase reaction.

The reaction products derived from the oligomerisation reaction as described herein, may be prepared using the disclosed catalyst by a homogeneous liquid phase reaction in the presence or absence of an inert solvent, and/or by slurry reaction where the catalyst is in a form that displays lithe or no solubility, and/or a two-phase liquid/liquid reaction, and/or a bulk phase reaction in which neat reagent and/or product olefins serve as the dominant medium, and/or gas phase reaction, using conventional equipment and contacting techniques.

The oligomerisation reaction may be carried out in a plant which includes reactor types known in the art. Examples of such reactors include, but are not limited to, batch reactors, semi-batch reactors and continuous reactors. The plant may include, in combination a) at least one reactor system, b) at least one inlet line into this reactor for olefin reactant and the catalyst system, c) effluent lines from this reactor for oligomerised reaction products, and d) at least one separator to separate the desired oligomerised reaction products which may include a recycle loop for solvents and/or reactants and/or products which may also serve as a temperature control mechanism.

According to another aspect of the present invention there is provided the use of an aliphatic liquid medium in a process for producing an oligomeric product by the oligomerisation of at least one olefinic compound in the form of an olefin or a compound including an olefinic moiety by contacting at least one olefinic compound with an oligomerisation catalyst in the aliphatic liquid medium at a reaction temperature of at least 50° C., wherein the catalyst comprises the combination of
 i) a source of a transition metal; and
 ii) a ligating compound of the formula

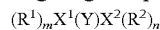

wherein:
 $X^1$ and $X^2$ are independently selected from the group consisting of
 N, P, As, Sb, Bi, O, S and Se;
 Y is a linking group between $X^1$ and $X^2$;
 m and n are independently 0, 1 or a larger integer; and
 $R^1$ and $R^2$ are independently hydrogen, a hydrocarbyl group or a heterohydrocarbyl group, and $R^1$ being the same or different when m>1, and $R^2$ being the same or different when n>1.

The invention will now be further described by means of the following non-limiting examples.

EXAMPLES

The individual components of the examples may conceivably be omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. The solvents isopar E and isopar C were obtained from ExxonMobil, they are mixtures of saturated aliphatic compounds. The solvent C7-C8 n-paraffins was obtained from Sasol, it is a mixture of linear paraffins (92.4% n-paraffins) containing 41.4% C7 hydrocarbons and 52.1% C8 hydrocarbons. All trialkylaluminium and aluminoxane compounds and solutions thereof were obtained from Crompton Gmbh, Akzo Nobel and Albemarle Corporation. In all the examples, the molar mass of methylaluminoxane (MAO and MAO-HS) was taken to be 58.016 g/mol, corresponding to the ($CH_3$—Al—O) unit, in order to calculate the molar quantities of MAO and MAO-HS used in the preparation of the catalysts described in the examples below. Similarly the molar mass of modified methylaluminoxane prepared from a 70:30 mixture of trimethylaluminium and tri-isobutylaluminium was taken as 70.7 g/mol corresponding to the ($Me_{0.70}isoBu_{0.30}$-Al—O) unit. Ethylene oligomerisation products were analysed by GC-MS and GC-FID.

The ligating compounds and chromium coordination complexes employed were prepared according to procedures disclosed in WO 2004/056479 and *J. Am. Chem. Soc.*, 2004, 126, 14712 and references cited therein.

Example 1 (Comparative)

Ethylene Tetramerisation Reaction Using Cr(acetylacetonate)$_3$, (phenyl)$_2$PN(isopropyl)P(phenyl)$_2$ and MAO in Toluene at 45° C./4500 kPa A solution of 12.8 mg of (phenyl)$_2$PN(isopropyl)P(phenyl)$_2$ (0.03 mmol) in 10 ml of toluene was added to a solution of 7.2 mg Cr(acetylacetonate)$_3$ (0.02 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 12 min, by discontinuing the ethylene feed to the reactor and cooling the reactor to below 10° C. After releasing the excess ethylene from the autoclave, the liquid contained in the autoclave was quenched with ethanol followed by 10% hydrochloric acid in water. Nonane was added as an internal standard for the analysis of the liquid phase by GC-FID. A small sample of the organic layer was dried over anhydrous sodium sulfate and then analysed by GC-FID. The remainder of the organic layer was filtered to isolate the solid products. These solid products were dried overnight in an oven at 100° C. and then weighed. The product mass was 62.98 g. The product distribution of this example is summarised in Table 1.

Example 2 (Comparative)

Ethylene Tetramerisation Reaction Using Cr(acetylacetonate)$_3$, (phenyl)$_2$PN(isopropyl)P(phenyl)$_2$ and MAO in Ethylbenzene at 45° C./4500 kPa A solution of 12.8 mg of (phenyl)$_2$PN(isopropyl)P(phenyl)$_2$ (0.03 mmol) in 10 ml of ethylbenzene was added to a solution of 7.2 mg Cr(acetylacetonate)$_3$ (0.02 mmol) in 10 ml ethylbenzene in a Schlenk vessel. The mixture was stirred for 5 min at ambient temperature and was then transferred to a 300 ml pressure reactor (autoclave) containing a mixture of ethylbenzene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 10 min, and the procedure of Example 1 above was employed. The product mass was 70.60 g. The product distribution of this example is summarised in Table 1.

Example 3 (Comparative)

Ethylene Tetramerisation Reaction Using Cr(acetylacetonate)$_3$, (phenyl)$_2$PN(isopropyl)P(phenyl)$_2$ and MAO in o-xylene at 45° C./4500 kPa A solution of 12.8 mg of (phenyl)$_2$PN(isopropyl)P(phenyl)$_2$ (0.03 mmol) in 10 ml of o-xylene was added to a solution of 7.2 mg Cr(acetylacetonate)$_3$ (0.02 mmol) in 10 ml o-xylene in a Schlenk vessel. The mixture was stirred for 5 min at ambient temperature and was then transferred to a 300 ml pressure reactor (autoclave) containing a mixture of o-xylene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 17 min, and the procedure of Example 1 above was employed. The product mass was 61.05 g. The product distribution of this example is summarised in Table 1.

Example 4 (Comparative)

Ethylene Tetramerisation Reaction Using Cr(acetylacetonate)$_3$, (phenyl)$_2$PN(isopropyl)P(phenyl)$_2$ and MAO in p-xylene at 45° C./4500 kPa A solution of 12.8 mg of (phenyl)$_2$PN(isopropyl)P(phenyl)$_2$ (0.03 mmol) in 10 ml of p-xylene was added to a solution of 7.2 mg Cr(acetylacetonate)$_3$ (0.02 mmol) in 10 ml p-xylene in a Schlenk vessel. The mixture was stirred for 5 min at ambient temperature and was then transferred to a 300 ml pressure reactor (autoclave) containing a mixture of p-xylene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 30 min, and the procedure of Example 1 above was employed. The product mass was 73.14 g. The product distribution of this example is summarised in Table 1.

Example 5 (Comparative)

Ethylene Tetramerisation Reaction Using Cr(acetylacetonate)$_3$, (phenyl)$_2$PN(isopropyl)P(phenyl)$_2$ and MAO in m-xylene at 45° C./4500 kPa A solution of 12.8 mg of (phenyl)$_2$PN(isopropyl)P(phenyl)$_2$ (0.03 mmol) in 10 ml of m-xylene was added to a solution of 7.2 mg Cr(acetylacetonate)$_3$ (0.02 mmol) in 10 ml m-xylene in a Schlenk vessel. The mixture was stirred for 5 min at ambient temperature and was then transferred to a 300 ml pressure reactor (autoclave) containing a mixture of m-xylene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 15 min, and the procedure of Example 1 above was employed. The product mass was 78.47 g. The product distribution of this example is summarised in Table 1.

Example 6 (Comparative)

Ethylene Tetramerisation Reaction Using Cr(acetylacetonate)$_3$, (phenyl)$_2$PN(isopropyl)P(phenyl)$_2$ and MAO in Diethylbenzene at 45° C./4500 kPa A solution of 12.8 mg of (phenyl)$_2$PN(isopropyl)P(phenyl)$_2$ (0.03 mmol) in 10 ml of diethylbenzene was added to a solution of 7.2 mg Cr(acetylacetonate)$_3$ (0.02 mmol) in 10 ml diethylbenzene in a Schlenk vessel. The mixture was stirred for 5 min at ambient temperature and was then transferred to a 300 ml pressure reactor (autoclave) containing a mixture of diethylbenzene (80 ml) and MAO (methylaluminoxane, 4 mmol) at 40° C. The pressure reactor was charged with ethylene after which the reactor temperature was controlled at 45° C., while the ethylene pressure was maintained at 4500 kPa. The reaction was terminated after 12 min, and the procedure of Example 1 above was employed. The product mass was 82.60 g. The product distribution of this example is summarised in Table 1.

Example 7 (Comparative)

Ethylene Tetramerisation Reaction Using Cr(acetylacetonate)$_3$, (phenyl)$_2$PN(isopropyl)P(phenyl)$_2$ and MAO in Cumene at 45° C./4500 kPa A solution of 12.0 mg of (phenyl)$_2$PN(isopropyl)P(phenyl)$_2$ (0.028 mmol) in 10 ml of cumene was added to a solution of 7.4 mg Cr(acetylacetonate)$_3$ (0.021 mmol) in 10 ml cumene in a Schlenk vessel. The mixture was stirred for 5 min at ambient temperature. This solution and a solution of MAO (methylaluminoxane, 4.0 mmol) was added via a burette to a 1000 ml pressure reactor (autoclave) containing cumene (180 ml) at 45° C. and being pressurised at 4000 kPa. After the addition, the ethylene pressure was maintained at 4500 kPa and the temperature controlled at 45° C. The reaction was terminated after 75 minutes, and the procedure of Example 1 above was employed. The mass of total product was 320.16 g. The product distribution of this example is summarised in Table 1.

Example 8 (Comparative)

Ethylene Tetramerisation Reaction Using Cr(acetylacetonate)$_3$, (phenyl)$_2$PN(isopropyl)P(phenyl)$_2$ and MAO in Cumene at 60° C./4500 kPa A solution of 12.0 mg of (phenyl)$_2$PN(isopropyl)P(phenyl)$_2$ (0.028 mmol) in 10 ml of cumene was added to a solution of 7.4 mg Cr(acetylacetonate)$_3$ (0.021 mmol) in 10 ml cumene in a Schlenk vessel. The mixture was stirred for 5 min at ambient temperature. This solution and a solution of MAO (methylaluminoxane, 4.0 mmol) was added via a burette to a 1000 ml pressure reactor (autoclave) containing cumene (180 ml) at 60° C. and being pressurised at 4000 kPa. After the addition, the ethylene pressure was maintained at 4500 kPa and the temperature controlled at 60° C. The reaction was terminated after 75 minutes, and the procedure of Example 1 above was employed. The mass of total product was 115.07 g. The product distribution of this example is summarised in Table 1.

Example 9 (Comparative)

Ethylene Tetramerisation Reaction Using CrCl$_3$(THF)$_3$, (phenyl)$_2$PN(isopropyl)P(phenyl)$_2$ and MAO in Toluene at 85° C./3000 kPa A solution of 30.9 mg of (phenyl)$_2$PN(isopropyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature. This solution and a solution of MAO (methylaluminoxane, 9.9 mmol) was added to a 300 ml pressure reactor (autoclave) containing toluene (70 ml) at 85° C. and being pressurised at 3000 kPa. After the addition, the ethylene pressure was maintained at 3000 kPa and the temperature controlled at 85° C. The reaction was terminated after 60 min, and the procedure of Example 1 above was employed. The product mass was 28.87 g. The product distribution of this example is summarised in Table 1.

Example 10 (Comparative)

Ethylene Tetramerisation Reaction Using CrCl$_3$(THF)$_3$, (phenyl)$_2$PN(isopropyl)P(phenyl)$_2$ and MAO in Toluene at 85° C./3000 kPa A solution of 29.8 mg of (phenyl)$_2$PN(isopropyl)P(phenyl)$_2$ (0.066 mmol) in 10 ml of toluene was added to a solution of 12.5 mg CrCl$_3$(THF)$_3$ (0.033 mmol) in 10 ml toluene in a Schlenk vessel. The mixture was stirred for 5 min at ambient temperature. This solution and a solution of MAO (methylaluminoxane, 9.9 mmol) was added to a 300 ml pressure reactor (autoclave) containing toluene (70 ml) at 85° C. and being pressurised at 3000 kPa. After the addition, the ethylene pressure was maintained at 3000 kPa and the temperature controlled at 85° C. The reaction was terminated after 60 min, and the procedure of Example 1 above was employed. The product mass was 22.35 g. The product distribution of this example is summarised in Table 1.

Example 11

Ethylene Tetramerisation Reaction Using Cr(acetylacetonate)$_3$, (phenyl)$_2$PN(isopropyl)P(phenyl)$_2$ and MAO in Cyclohexane at 60° C./4500 kPa A solution of 5.8 mg of (phenyl)$_2$PN(isopropyl)P(phenyl)$_2$ (0.014 mmol) in 10 ml of cyclohexane was added to a solution of 3.5 mg Cr(acetylacetonate)$_3$ (0.01 mmol) in 10 ml cyclohexane in a Schlenk vessel. The mixture was stirred for 5 min at ambient temperature. This solution and a solution of MAO (methylaluminoxane, 2.0 mmol) was added via a burette to a 1000 ml pressure reactor (autoclave) containing cyclohexane (180 ml) at 60° C. and being pressurised at 4000 kPa. After the addition, the ethylene pressure was maintained at 4500 kPa and the temperature controlled at 60° C. The reaction was terminated after 60 min, and the procedure of Example 1 above was employed. The product mass was 337.04 g. The product distribution of this example is summarised in Table 1.

Example 12

Ethylene Tetramerisation Reaction Using Cr(acetylacetonate)$_3$, (phenyl)$_2$PN(isopropyl)P(phenyl)$_2$ and MMAO in Cyclohexane at 60° C./4500 kPa A solution of 5.8 mg of (phenyl)$_2$PN(isopropyl)P(phenyl)$_2$ (0.014 mmol) in 10 ml of cyclohexane was added to a solution of 3.5 mg Cr(acetylacetonate)$_3$ (0.01 mmol) in 10 ml cyclohexane in a Schlenk vessel. The mixture was stirred for 5 min at ambient temperature. This solution and a solution of MMAO-3A (modified methylaluminoxane, 2.0 mmol) was added via a burette to a 1000 ml pressure reactor (autoclave) containing cyclohexane (180 ml) at 60° C. and being pressurised at 4000 kPa. After the addition, the ethylene pressure was maintained at 4500 kPa and the temperature controlled at 60° C. The reaction was terminated after 40 min, and the procedure of Example 1 above was employed. The product mass was 328.70 g. The product distribution of this example is summarised in Table 1.

Example 13

Ethylene Tetramerisation Reaction Using Cr(acetylacetonate)$_3$, (phenyl)$_2$PN(isopropyl)P(phenyl)$_2$ and MMAO in Isopar C at 65° C./4500 kPa A solution of 2.1 mg of (phenyl)$_2$PN(isopropyl)P(phenyl)$_2$ (0.005 mmol) in 5 ml of isopar C was added to a solution of 1.8 mg Cr(acetylacetonate)$_3$ (0.005 mmol) in 5 ml isopar C in a Schlenk vessel. MMAO-3A (modified methylaluminoxane, 2.4 mmol) was added and the mixture was immediately transferred to a 300 ml pressure reactor (autoclave) containing isopar C (90 ml) at 65° C. The pressure reactor was charged with ethylene after which the reactor temperature was controlled at 65° C., while the ethylene pressure was maintained at 4500 kPa. The reaction was terminated after 32 min, and the procedure of Example 1 above was employed. The product mass was 80.5 g. The product distribution of this example is summarised in Table 1.

Example 14

Ethylene Tetramerisation Reaction Using Cr(acetylacetonate)$_3$, (phenyl)$_2$PN(isopropyl)P(phenyl)$_2$ and MMAO in Isopar E at 60° C./4500 kPa A solution of 4.2 mg of (phenyl)$_2$PN(isopropyl)P(phenyl)$_2$ (0.01 mmol) in 5 ml of isopar E was added to a solution of 3.5 mg Cr(acetylacetonate)$_3$ (0.01 mmol) in 5 ml isopar E in a Schlenk vessel. MMAO-3A (modified methylaluminoxane, 2.8 mmol) was added and the mixture was immediately transferred to a 300 ml pressure reactor (autoclave) containing isopar E (90 ml) at 55° C. The pressure reactor was charged with ethylene after which the reactor temperature was controlled at 60° C., while the ethylene pressure was maintained at 4500 kPa. The reaction was terminated after 8.25 min, and the procedure of Example 1 above was employed. The product mass was 70.63 g. The product distribution of this example is summarised in Table 1.

Example 15

Ethylene Tetramerisation Reaction Using Cr(acetylacetonate)$_3$, (phenyl)$_2$PN(isopropyl)P(phenyl)$_2$ and MMAO in C$_7$-C$_8$ n-paraffins (Sasol Commercial Product) at 60° C./4500 kPa A solution of 4.2 mg of (phenyl)$_2$PN(isopropyl)P(phenyl)$_2$ (0.01 mmol) in 5 ml of C7-C8 n-paraffins was added to a solution of 3.5 mg Cr(acetylacetonate)$_3$ (0.01 mmol) in 5 ml C$_7$-C$_8$ n-paraffins in a Schlenk vessel. MMAO-3A (modified methylaluminoxane, 2.8 mmol) was added and the mixture was immediately transferred to a 300 ml pressure reactor (autoclave) containing C7-C8 n-paraffins (90 ml) at 55° C. The pressure reactor was charged with ethylene after which the reactor temperature was controlled at 60° C., while the ethylene pressure was maintained at 4500 kPa. The reaction was terminated after 16.5 min, and the procedure of Example 1 above was employed. The product mass was 69.3 g. The product distribution of this example is summarised in Table 1.

Example 16

Ethylene Tetramerisation Reaction Using Cr(acetylacetonate)$_3$, (phenyl)$_2$PN(isopropyl)P(phenyl)$_2$ and MMAO in Methylcyclohexane at 80° C./4500 kPa A solution of 5.8 mg of (phenyl)$_2$PN(isopropyl)P(phenyl)$_2$ (0.014 mmol) in 10 ml of methylcyclohexane was added to a solution of 3.5 mg Cr(acetylacetonate)$_3$ (0.01 mmol) in 10 ml methylcyclohexane in a Schlenk vessel. The mixture was stirred for 5 min at ambient temperature. This solution and a solution of MMAO-3A (modified methylaluminoxane, 2.0 mmol) was added via a burette to a 1000 ml pressure reactor (autoclave) containing methylcyclohexane (180 ml) at 80° C. and being pressurised at 4000 kPa. After the addition, the ethylene pressure was maintained at 4500 kPa and the temperature controlled at 80° C. The reaction was terminated after 60 min, and the procedure of Example 1 above was employed. The product mass was 161.57 g. The product distribution of this example is summarised in Table 1.

Example 17

Ethylene Tetramerisation Reaction Using Cr(acetylacetonate)$_3$, (phenyl)$_2$PN(isopropyl)P(phenyl)$_2$ and MMAO in Methylcyclohexane at 60° C./4500 kPa A solution of 2.14 mg of (phenyl)$_2$PN(isopropyl)P(phenyl)$_2$ (0.005 mmol) in 10 ml of cyclohexane was added to a solution of 1.8 mg Cr(acetylacetonate)$_3$ (0.005 mmol) in 10 ml methylcyclohexane in a Schlenk vessel. The mixture was stirred for 5 min at ambient temperature. This solution was mixed with a solution of MMAO-3A (modified methylaluminoxane, 1.4 mmol) and immediately added via a burette to a 1000 ml pressure reactor (autoclave) containing methylcyclohexane (180 ml) at 60° C. and being pressurised at 4000 kPa. After the addition, the ethylene pressure was maintained at 4500 kPa and the temperature controlled at 60° C. The reaction was terminated after 60 min, and the procedure of Example 1 above was employed. The product mass was 307.86 g. The product distribution of this example is summarised in Table 1.

Example 18

Ethylene Tetramerisation Reaction Using Cr(acetylacetonate)$_3$, (phenyl)$_2$PN(isopropyl)P(phenyl)$_2$ and MMAO in Methylcyclohexane/Toluene at 60° C./4500 kPa A solution of 2.14 mg of (phenyl)$_2$PN(isopropyl)P(phenyl)$_2$ (0.005 mmol) in 10 ml of cyclohexane was added to a solution of 1.8 mg Cr(acetylacetonate)$_3$ (0.005 mmol) in 8 ml methylcyclohexane and 2 ml of toluene in a Schlenk vessel. The mixture was stirred for 5 min at ambient temperature. This solution was mixed with a solution of MMAO-3A (modified methylaluminoxane, 1.4 mmol) and immediately added via a burette to a 1000 ml pressure reactor (autoclave) containing methylcyclohexane (180 ml) at 60° C. and being pressurised at 4000 kPa. After the addition, the ethylene pressure was maintained at 4500 kPa and the temperature controlled at 60° C. The reaction was terminated after 60 min, and the procedure of Example 1 above was employed. The product mass was 170.16 g. The product distribution of this example is summarised in Table 1.

Example 19

Ethylene Tetramerisation Reaction Using Cr(acetylacetonate)$_3$, (phenyl)$_2$PN(isopropyl)P(phenyl)$_2$ and MMAO in Methylcyclohexane at 80° C./8000 kPa A solution of 11.5 mg of (phenyl)$_2$PN(isopropyl)P(phenyl)$_2$ (0.027 mmol) in 10 ml of methylcyclohexane was added to a solution of 7 mg Cr(acetylacetonate)$_3$ (0.02 mmol) in 10 ml methylcyclohexane in a Schlenk vessel. The mixture was stirred for 5 min at ambient temperature and was then transferred to a 300 ml pressure reactor (autoclave) containing a mixture of methylcyclohexane (80 ml) and MMAO-3A (modified methylaluminoxane, 4 mmol) at 75° C. The pressure reactor was charged with ethylene after which the reactor temperature was controlled at 80° C., while the ethylene pressure was maintained at 8000 kPa. The reaction was terminated after 5 min, and the procedure of Example 1 above was employed. The product mass was 80.68 g. The product distribution of this example is summarised in Table 1.

Example 20

Ethylene Tetramerisation Reaction Using Cr(acetylacetonate)$_3$, (phenyl)$_2$PN(isopropyl)P(phenyl)$_2$ and MMAO in Methylcyclohexane at 60° C./8000 kPa A solution of 11.5 mg of (phenyl)$_2$PN(isopropyl)P(phenyl)$_2$ (0.027 mmol) in 10 ml of methylcyclohexane was added to a solution of 7 mg Cr(acetylacetonate)$_3$ (0.02 mmol) in 10 ml methylcyclohexane in a Schlenk vessel. The mixture was stirred for 5 min at ambient temperature and was then transferred to a 300 ml pressure reactor (autoclave) containing a mixture of methylcyclohexane (80 ml) and MMAO-3A (modified methylaluminoxane, 4 mmol) at 55° C. The pressure reactor was charged with ethylene after which the reactor temperature was controlled at 60° C., while the ethylene pressure was maintained at 8000 kPa. The reaction was terminated after 5.5 min, and the procedure of Example 1 above was employed. The product mass was 57.83 g. The product distribution of this example is summarised in Table 1.

Example 21.1

Preparation of the Complexes [(phenyl$_2$P)$_2$N(R)CrCl$_3$]$_2$

The complexes [(phenyl$_2$P)$_2$N(R)CrCl$_3$]$_2$ (R=isopropyl, 1,2-dimethylpropyl, 2-methylcyclohexyl) were prepared according to the preparation of [(phenyl$_2$P)$_2$N(phenyl)CrCl$_3$]$_2$ as described in J. Am. Chem. Soc. 2004, 126(45), 14712.

Example 21

Ethylene Tetramerisation Reaction Using [(phenyl$_2$P)$_2$N(isopropyl)CrCl$_3$]$_2$ and MMAO in Methylcyclohexane at 100° C./5000 kPa A suspension of 11.7 mg of [(phenyl$_2$P)$_2$N(isopropyl)CrCl$_3$]$_2$ (0.010 mmol) in 10 ml of methylcyclohexane was transferred to a 300 ml pressure reactor (autoclave) containing a mixture of methylcyclohexane (90 ml) and MMAO-3A (modified methylaluminoxane, 3.8 mmol) at 100° C. The pressure reactor was charged with ethylene after which the reactor temperature was controlled at 100° C., while the ethylene pressure was maintained at 5000 kPa. The reaction was terminated after 12 min, and the procedure of Example 1 above was employed. The product mass was 71.5 g. The product distribution of this example is summarised in Table 1.

Example 22

Ethylene Tetramerisation Reaction Using Cr(acetylacetonate)$_3$, (phenyl)$_2$PN(1,2-dimethylpropyl)P(phenyl)$_2$ and MMAO-3A in Toluene at 45° C./4500 kPa A solution of 4.6 mg of (phenyl)$_2$PN(1,2-dimethylpropyl)P(phenyl)$_2$ (0.01 mmol) in 10 ml of toluene was added to a solution of 3.5 mg Cr(acetylacetonate)$_3$ (0.01 mmol) in 10 ml toluene in a Schlenk vessel. This solution was mixed with a solution of MMAO-3A (modified methylaluminoxane, 4.8 mmol) and immediately added to a 300 ml pressure reactor (autoclave) containing toluene (80 ml) at 45° C. The pressure reactor was charged with ethylene after which the reactor temperature was controlled at 45° C., while the ethylene pressure was maintained at 4500 kPa. The reaction was terminated after 30 min, and the procedure of Example 1 above was employed. The product mass was 17.2 g. The product distribution of this example is summarised in Table 1.

Example 23

Ethylene Tetramerisation Reaction Using Cr(acetylacetonate)$_3$, (phenyl)$_2$PN(1,2-dimethylpropyl)P(phenyl)$_2$ and MMAO in Methylcyclohexane at 60° C./7000 kPa A solution of 2.3 mg of (phenyl)$_2$PN(1,2-dimethylpropyl)P(phenyl)$_2$ (0.005 mmol) in 10 ml of cyclohexane was added to a solution of 1.8 mg Cr(acetylacetonate)$_3$ (0.005 mmol) in 10 ml methylcyclohexane in a Schlenk vessel. The mixture was stirred for 5 min at ambient temperature. This solution was mixed with a solution of MMAO-3A (modified methylaluminoxane, 1.4 mmol) and immediately added via a burette to a 1000 ml pressure reactor (autoclave) containing methylcyclohexane (180 ml) at 60° C. and being pressurised at 6500 kPa. After the addition, the ethylene pressure was maintained at 7000 kPa and the temperature controlled at 60° C. The reaction was terminated after 13 min, and the procedure of Example 1 above was employed. The product mass was 349.4 g. The product distribution of this example is summarised in Table 1.

Example 24

Ethylene Tetramerisation Reaction Using [(phenyl$_2$P)$_2$N(1,2-dimethylpropyl)CrCl$_3$]$_2$ and MMAO in Methylcyclohexane at 80° C./5000 kPa A suspension of [(phenyl$_2$P)$_2$N(1,2-dimethylpropyl)CrCl$_3$]$_2$ (1.2 mg, 0.002 mmol of Cr) in 10 ml of methylcyclohexane was transferred to a 300 ml pressure reactor (autoclave) containing a mixture of methylcyclohexane (90 ml) and MMAO-3A (modified methylaluminoxane, 1.9 mmol) at 80° C. The pressure reactor was charged with ethylene after which the reactor temperature was controlled at 80° C., while the ethylene pressure was maintained at 5000 kPa. The reaction was terminated after 20 min, and the procedure of Example 1 above was employed. The product mass was 59.69 g. The product distribution of this example is summarised in Table 1.

Example 25

Ethylene Tetramerisation Reaction Using Cr(acetylacetonate)$_3$, (phenyl)$_2$PN(2-methylcyclohexyl)P(phenyl)$_2$ and MMAO-3A in Toluene at 60° C./5000 kPa A solution of 2.4 mg of (phenyl)$_2$PN(2-methylcyclohexyl)P(phenyl)$_2$ (0.005 mmol) in 10 ml of toluene was added to a solution of 1.8 mg Cr(acetylacetonate)$_3$ (0.005 mmol) in 10 ml toluene in a Schlenk vessel. This solution was mixed with a solution of MMAO-3A (modified methylaluminoxane, 2.4 mmol) and immediately added to a 300 ml pressure reactor (autoclave) containing toluene (80 ml) at 60° C. The pressure reactor was charged with ethylene after which the reactor temperature was controlled at 60° C., while the ethylene pressure was maintained at 5000 kPa. The reaction was terminated after 30 min, and the procedure of Example 1 above was employed. The product mass was 2.2 g. The product distribution of this example is summarised in Table 1.

Example 26

Ethylene Tetramerisation Reaction Using Cr(acetylacetonate)$_3$, (phenyl)$_2$PN(2-methylcyclohexyl)P(phenyl)$_2$ and MMAO in Methylcyclohexane at 60° C./7000 kPa A solution of 2.4 mg of (phenyl)$_2$PN(2-methylcyclohexyl)P(phenyl)$_2$ (0.005 mmol) in 10 ml of cyclohexane was added to a solution of 1.8 mg Cr(acetylacetonate)$_3$ (0.005 mmol) in 10 ml methylcyclohexane in a Schlenk vessel. The mixture was stirred for 5 min at ambient temperature. This solution was mixed with a solution of MMAO-3A (modified methylaluminoxane, 1.4 mmol) and immediately added via a burette to a 1000 ml pressure reactor (autoclave) containing methylcyclohexane (180 ml) at 60° C. and being pressurised at 6500 kPa. After the addition, the ethylene pressure was maintained at 7000 kPa and the temperature controlled at 60° C. The reaction was terminated after 27 min, and the procedure of Example 1 above was employed. The product mass was 313.5 g. The product distribution of this example is summarised in Table 1.

Example 27

Ethylene Tetramerisation Reaction Using [(phenyl$_2$P)$_2$N(2-methylcyclohexyl)CrCl$_3$]$_2$ and MMAO in Methylcyclohexane at 80° C./5000 kPa A suspension of 12.8 mg of [(phenyl$_2$P)$_2$N(2-methylcyclohexyl)CrCl$_3$]$_2$ (0.010 mmol) in 10 ml of methylcyclohexane was transferred to a 300 ml pressure reactor (autoclave) containing a mixture of methylcyclohexane (90 ml) and MMAO-3A (modified methylaluminoxane, 3.8 mmol) at 80° C. The pressure reactor was charged with ethylene after which the reactor temperature was controlled at 80° C., while the ethylene pressure was maintained at 5000 kPa. The reaction was terminated after 45 min, and the procedure of Example 1 above was employed. The product mass was 72.9 g. The product distribution of this example is summarised in Table 1.

Example 28

Ethylene Tetramerisation Reaction Using CrCl$_3$(THF)$_3$, (phenyl)$_2$PN(cyclohexylethyl)P(phenyl)$_2$ and MAO in Toluene at 45° C./3000 kPa A solution of 32.5 mg of (phenyl)$_2$PN(cyclohexylethyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 45° C. The pressure reactor was charged with ethylene after which the reactor temperature was controlled at 45° C., while the ethylene pressure was maintained at 3000 kPa. The reaction was terminated after 60 min, and the procedure of Example 1 above was employed. The product mass was 15.6 g. The product distribution of this example is summarised in Table 1.

Example 29

Ethylene Tetramerisation Reaction Using Cr(acetylacetonate)$_3$, (phenyl)$_2$PN(cyclohexylethyl)P(phenyl)$_2$ and MMAO in Methylcyclohexane at 80° C./5700 kPa A solution of 6.7 mg of (phenyl)$_2$PN(cyclohexylethyl)P(phenyl)$_2$ (0.014 mmol) in 10 ml of methylcyclohexane was added to a solution of 3.5 mg Cr(acetylacetonate)$_3$ (0.01 mmol) in 10 ml methylcyclohexane in a Schlenk vessel. The mixture was stirred for 5 min at ambient temperature. This solution and a solution of MMAO-3A (modified methylaluminoxane, 2.0 mmol) was added via a burette to a 1000 ml pressure reactor (autoclave) containing methylcyclohexane (180 ml) at 80° C. and being pressurised at 5700 kPa. After the addition, the ethylene pressure was maintained at 5700 kPa and the temperature controlled at 80° C. The reaction was terminated after 40 min, and the procedure of Example 1 above was employed. The product mass was 257.2 g. The product distribution of this example is summarised in Table 1.

Example 30

Ethylene Tetramerisation Reaction Using Cr(acetylacetonate)$_3$, (phenyl)$_2$PN($^i$propyl)P(phenyl)$_2$ and MAO-HS in Methylcyclohexane at 60° C./4500 kPa A solution of 5.8 mg of (phenyl)$_2$PN($^i$propyl)P(phenyl)$_2$ (0.014 mmol) in 10 ml of methylcyclohexane was added to a solution of 3.5 mg Cr(acetylacetonate)$_3$ (0.01 mmol) in 10 ml methylcyclohexane in a Schlenk vessel. The mixture was stirred for 5 min at ambient temperature. This solution and a solution of MAO-HS (methylaluminoxane HS from Albemarle, 2.5 mmol) was added to a 300 ml pressure reactor (autoclave) containing methylcyclohexane (180 ml) at 60° C. and being pressurised at 4500 kPa. After the addition, the ethylene pressure was maintained at 4500 kPa and the temperature controlled at 60° C. The reaction was terminated after 45 minutes and the procedure of Example 1 above was employed. The mass of total product was 165.39 g. The product distribution of this example is summarised in Table 1.

Example 31 (Comparative)

Ethylene Tetramerisation Reaction Using Cr(acetylacetonate)$_3$, (phenyl)$_2$PN($^i$propyl)P(phenyl)$_2$ and MAO-HS in Toluene at 45° C./4500 kPa A solution of 11.5 mg of (phenyl)$_2$PN($^i$propyl)P(phenyl)$_2$ (0.028 mmol) in 10 ml of toluene was added to a solution of 7.0 mg Cr(acetylacetonate)$_3$ (0.02 mmol) in 10 ml toluene in a Schlenk vessel. The mixture was stirred for 5 min at ambient temperature. This solution and a solution of MAO-HS (methylaluminoxane HS from Albemarle, 5 mmol) was added to a 300 ml pressure reactor (autoclave) containing toluene (80 ml) at 45° C. and being pressurised at 4500 kPa. After the addition, the ethylene pressure was maintained at 4500 kPa and the temperature controlled at 45° C. The reaction was terminated after 14 minutes and the procedure of Example 1 above was employed. The mass of total product was 70.02 g. The product distribution of this example is summarised in Table 1.

Example 32

Ethylene Tetramerisation Reaction Using CrCl$_3$(THF)$_3$, (phenyl)$_2$PN(phenyl)P(phenyl)$_2$ and MAO in Toluene at 85° C./3000 kPa A solution of 30.5 mg of (phenyl)$_2$PN(phenyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 80° C. The pressure reactor was charged with ethylene after which the reactor temperature was controlled at 85° C., while the ethylene pressure was maintained at 3000 kPa. The reaction was terminated after 60 min, and the procedure of Example 1 above was employed. The product mass was 15.05 g. The product distribution of this example is summarised in Table 1.

Example 33

Ethylene Tetramerisation Reaction Using Cr(acetylacetonate)$_3$, (phenyl)$_2$PN(phenyl)P(phenyl)$_2$ and MMAO-3A in Methylcyclohexane at 60° C./5000 kPa A solution of 4.6 mg of (phenyl)$_2$PN(phenyl)P(phenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 60° C. The pressure reactor was charged with ethylene after which the reactor temperature was controlled at 60° C., while the ethylene pressure was maintained at 5000 kPa. The reaction was terminated after 12 min, and the procedure of Example 1 above was employed. The product mass was 79.7 g. The product distribution of this example is summarised in Table 1.

Example 34

Ethylene Tetramerisation Reaction Using CrCl$_3$(THF)$_3$, (phenyl)$_2$PN(p-NO$_2$-phenyl)P(phenyl)$_2$ and MAO in Toluene at 65° C./3000 kPa A solution of 33.4 mg of (phenyl)$_2$PN(p-NO$_2$-phenyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 60° C. The pressure reactor was charged with ethylene after which the reactor temperature was controlled at 65° C., while the ethylene pressure was maintained at 3000 kPa. The reaction was terminated after 120 min, and the procedure of Example 1 above was employed. The product mass was 15.3 g. The product distribution of this example is summarised in Table 1.

Example 35

Ethylene Tetramerisation Reaction using CrCl$_3$(THF)$_3$, (phenyl)$_2$PN(p-NO$_2$-phenyl)P(phenyl)$_2$ and MAO in Toluene at 85° C./3000 kPa A solution of 33.4 mg of (phenyl)$_2$PN(p-NO$_2$-phenyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 80° C. The pressure reactor was charged with ethylene after which the reactor temperature was controlled at 85° C., while the ethylene pressure was maintained at 3000 kPa. The reaction was terminated after 60 min, and the procedure of Example 1 above was employed. The product mass was 10.4 g. The product distribution of this example is summarised in Table 1.

Example 36

Ethylene Tetramerisation Reaction using Cr(acetylacetonate)$_3$, (phenyl)$_2$PN(p-NO$_2$-phenyl)P(phenyl)$_2$ and MMAO-3A in Methylcyclohexane at 60° C./5000 kPa A solution of 5.1 mg of (phenyl)$_2$PN(p-NO$_2$-phenyl)P(phenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 60° C. The pressure reactor was charged with ethylene after which the reactor temperature was controlled at 60° C., while the ethylene pressure was maintained at 5000 kPa. The reaction was terminated after 13 min, and the procedure of Example 1 above was employed. The product mass was 105.1 g. The product distribution of this example is summarised in Table 1.

Example 37

Ethylene Tetramerisation Reaction Using CrCl$_3$(THF)$_3$, (phenyl)$_2$PN(p-$^t$butyl-phenyl)P(phenyl)$_2$ and MAO in Toluene at 65° C./3000 kPa A solution of 34.2 mg of (phenyl)$_2$PN(4-$^t$butyl-phenyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 60° C. The pressure reactor was charged with ethylene after which the reactor temperature was controlled at 65° C., while the ethylene pressure was maintained at 3000 kPa. The reaction was terminated after 180 min, and the procedure of Example 1 above was employed. The product mass was 62.2 g. The product distribution of this example is summarised in Table 1.

Example 38

Ethylene Tetramerisation Reaction Using CrCl$_3$(THF)$_3$, (phenyl)$_2$PN(p-$^t$butyl-phenyl)P(phenyl)$_2$ and MAO in Toluene at 85° C./3000 kPa A solution of 34.2 mg of (phenyl)$_2$PN(p-$^t$butyl-phenyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 80° C. The pressure reactor was charged with ethylene after which the reactor temperature was controlled at 85° C., while the ethylene pressure was maintained at 3000 kPa. The reaction was terminated after 180 min, and the procedure of Example 1 above was employed. The product mass was 9.2 g. The product distribution of this example is summarised in Table 1.

Example 39

Ethylene Tetramerisation Reaction Using Cr(acetylacetonate)$_3$, (phenyl)$_2$PN(p-$^t$butyl-phenyl)P(phenyl)$_2$ and MMAO-3A in Methylcyclohexane at 60° C./5000 kPa A solution of 5.2 mg of (phenyl)$_2$PN(p-$^t$butyl-phenyl)P(phenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 60° C. The pressure reactor was charged with ethylene after which the reactor temperature was controlled at 60° C., while the ethylene pressure was maintained at 5000 kPa. The reaction was terminated after 9 min, and the procedure of Example 1 above was employed. The product mass was 89.5 g. The product distribution of this example is summarised in Table 1.

Example 40

Ethylene Tetramerisation Reaction Using CrCl$_3$(THF)$_3$, (phenyl)$_2$PN(benzyl)P(phenyl)$_2$ and MAO in Toluene at 65° C./3000 kPa A solution of 31.4 mg of (phenyl)$_2$PN(benzyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 60° C. The pressure reactor was charged with ethylene after which the reactor temperature was controlled at 65° C., while the ethylene pressure was maintained at 3000 kPa. The reaction was terminated after 180 min, and the procedure of Example 1 above was employed. The product mass was 22.1 g. The product distribution of this example is summarised in Table 1.

Example 41

Ethylene Tetramerisation Reaction Using CrCl$_3$(THF)$_3$, (phenyl)$_2$PN(benzyl)P(phenyl)$_2$ and MAO in Toluene at 85° C./3000 kPa A solution of 31.4 mg of (phenyl)$_2$PN(benzyl)P(phenyl)$_2$ (0.066 mmol) in 10 ml of toluene was added to a solution of 12.6 mg CrCl$_3$(THF)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (70 ml) and MAO (methylaluminoxane, 9.9 mmol) at 80° C. The pressure reactor was charged with ethylene after which the reactor temperature was controlled at 85° C., while the ethylene pressure was maintained at 3000 kPa. The reaction was terminated after 60 min, and the procedure of Example 1 above was employed. The product mass was 13.0 g. The product distribution of this example is summarised in Table 1.

Example 42

Ethylene Tetramerisation Reaction Using Cr(acetylacetonate)$_3$, (phenyl)$_2$PN(benzyl)P(phenyl)$_2$ and MMAO-3A in Methylcyclohexane at 60° C./5000 kPa A solution of 4.8 mg of (phenyl)$_2$PN(benzyl)P(phenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 60° C. The pressure reactor was charged with ethylene after which the reactor temperature was controlled at 60° C., while the ethylene pressure was maintained at 5000 kPa. The reaction was terminated after 9 min, and the procedure of Example 1 above was employed. The product mass was 83.1 g. The product distribution of this example is summarised in Table 1.

Example 43

Ethylene Tetramerisation Reaction Using Cr(acetylacetonate)$_3$, (p-biphenyl)$_2$PN(methyl)P(p-biphenyl)$_2$ and MAO in Toluene at 65° C./3000 kPa A solution of 47.0 mg of (p-biphenyl)$_2$PN(methyl)P(p-biphenyl)$_2$ (0.066 mmol) in 10 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 3000 kPa. The reaction was terminated after 30 min, and the procedure of Example 1 above was employed. The product mass was 26.4 g. The product distribution of this example is summarised in Table 1.

Example 44

Ethylene Tetramerisation Reaction Using Cr(acetylacetonate)$_3$, (p-biphenyl)$_2$PN(methyl)P(p-biphenyl)$_2$ and MMAO-3A in Methylcyclohexane at 60° C./5000 kPa A solution of 4.0 mg of (p-biphenyl)$_2$PN(methyl)P(p-biphenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 60° C. The pressure reactor was charged with ethylene after which the reactor temperature was controlled at 60° C., while the ethylene pressure was maintained at 5000 kPa. The reaction was terminated after 28 min, and the procedure of Example 1 above was employed. The product mass was 12.2 g. The product distribution of this example is summarised in Table 1.

Example 45

Ethylene Tetramerisation Reaction Using Cr(acetylacetonate)$_3$, (p-methoxyphenyl)$_2$PN(methyl)P(p-methoxyphenyl)$_2$ and MAO in Toluene at 65° C./3000 kPa A solution of 30.0 mg of (p-methoxyphenyl)$_2$PN(methyl)P(p-methoxyphenyl)$_2$ (0.066 mmol) in 10 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 60° C. The pressure reactor was charged with ethylene after which the reactor temperature was controlled at 65° C., while the ethylene pressure was maintained at 3000 kPa. The reaction was terminated after 30 min, and the procedure of Example 1 above was employed. The product mass was 38.7 g. The product distribution of this example is summarised in Table 1.

Example 46

Ethylene Tetramerisation Reaction Using Cr(acetylacetonate)$_3$, (p-methoxyphenyl)$_2$PN(methyl)P(p-methoxyphenyl)$_2$ and MMAO-3A in Methylcyclohexane at 65° C./3000 kPa A solution of 5.2 mg of (p-methoxyphenyl)$_2$PN(methyl)P(p-methoxyphenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 65° C. The pressure reactor was charged with ethylene after which the reactor temperature was controlled at 65° C., while the ethylene pressure was maintained at 3000 kPa. The reaction was terminated after 40 min, and the procedure of Example 1 above was employed. The product mass was 60.8 g. The product distribution of this example is summarised in Table 1.

Example 47

Ethylene Tetramerisation Reaction Using Cr(acetylacetonate)$_3$, (o-ethylphenyl)$_2$PN(methyl)P(o-ethylphenyl)$_2$ and MAO in Toluene at 45° C./4500 kPa A solution of 33.7 mg of (o-ethylphenyl)$_2$PN(methyl)P(o-ethylphenyl)$_2$ (0.066 mmol) in 5 ml of toluene was added to a solution of 11.5 mg Cr (acetylacetonate)$_3$ (0.033 mmol) in 15 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 4.95 mmol) at 45° C. The pressure reactor was charged with ethylene after which the reactor temperature was controlled at 45° C., while the ethylene pressure was maintained at 4500 kPa. The reaction was terminated after 10 min, and the procedure of Example 1 above was employed. The product mass was 17.7 g. The product distribution of this example is summarised in Table 1.

Example 48

Ethylene Tetramerisation Reaction Using Cr(acetylacetonate)$_3$, (o-ethylphenyl)$_2$PN(methyl)P(o-ethylphenyl)$_2$ and MMAO in Methylcyclohexane at 55° C./2000 kPa A solution of 1.28 mg of (o-ethylphenyl)$_2$PN(methyl)P(o-ethylphenyl)$_2$ (0.0025 mmol) in 5 ml of methylcyclohexane was added to a solution of 0.88, mg Cr(acetylacetonate)$_3$ (0.0025 mmol) in 5 ml methylcyclohexane in a Schlenk vessel. This solution was mixed with a solution of MMAO-3A (modified methylaluminoxane, 0.7 mmol) and immediately added to a 300 ml pressure reactor (autoclave) containing methylcyclohexane (80 ml) at 55° C. The pressure reactor was charged with ethylene after which the reactor temperature was controlled at 55° C., while the ethylene pressure was maintained at 2000 kPa. The reaction was terminated after 12 min, and the procedure of Example 1 above was employed. The product mass was 91.6 g. The product distribution of this example is summarised in Table 1.

Example 49

Ethylene Tetramerisation Reaction Using Cr(acetylacetonate)$_3$, (o-methoxyphenyl)$_2$PN(methyl)P(o-methoxyphenyl)$_2$ and MAO in Toluene at 45° C./4500 kPa A solution of 30.0 mg of (o-methoxyphenyl)$_2$PN(methyl)P(o-methoxyphenyl)$_2$ (0.066 mmol) in 10 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was controlled at 45° C., while the ethylene pressure was maintained at 4500 kPa. The reaction was terminated after 30 min, and the procedure of Example 1 above was employed. The product mass was 68.7 g. The product distribution of this example is summarised in Table 1.

Example 50

Ethylene Tetramerisation Reaction Using Cr(acetylacetonate)$_3$, (o-methoxyphenyl)$_2$PN(methyl)P(o-methoxyphenyl)$_2$ and MMAO-3A in Methylcyclohexane at 90° C./3500 kPa A solution of 5.2 mg of (o-methoxyphenyl)$_2$PN(methyl)P (o-methoxyphenyl)$_2$ (0.01 mmol) in 10 ml of methylcyclohexane was added to a solution of 3.5 mg Cr(acetylacetonate)$_3$ (0.01 mmol) in 10 ml methylcyclohexane in a Schlenk vessel. This solution was mixed with a solution of MMAO-3A (modified methylaluminoxane, 4.8 mmol) and immediately added to a 300 ml pressure reactor (autoclave) containing methylcyclohexane (80 ml) at 90° C. The pressure reactor was charged with ethylene after which the reactor temperature was controlled at 90° C., while the ethylene pressure was maintained at 3500 kPa. The reaction was terminated after 5 min, and the procedure of Example 1 above was employed. The product mass was 103.2 g. The product distribution of this example is summarised in Table 1.

Example 51

Ethylene Tetramerisation Reaction Using Cr(2-ethylhexanoate)$_3$, (ethyl)$_2$PN(methyl)P(ethyl)$_2$ and MAO in Toluene at 45° C./4000 kPa A solution of Cr(2-ethylhexanoate)$_3$ (0.002M in toluene, 10 ml, 0.02 mmol) and a solution of (ethyl)$_2$PN(methyl)P (ethyl)$_2$ (0.005M in toluene, 4.1 ml, 0.0205 mmol) were added to a 300 ml pressure reactor (autoclave) containing a mixture of toluene (100 ml) and MAO (methylaluminoxane, 6.0 mmol) at 45° C. The pressure reactor was charged with ethylene after which the reactor temperature was controlled at 45° C., while the ethylene pressure was maintained at 4000 kPa. The reaction was terminated after 30 min, and the procedure of Example 1 above was employed. The product mass was 2.3 g. The product distribution of this example is summarised in Table 1.

Example 52

Ethylene Tetramerisation Reaction Using Cr(acetylacetonate)$_3$, (ethyl)$_2$PN(methyl)P(ethyl)$_2$ and MMAO-3A in Methylcyclohexane at 60° C./5000 kPa A solution of 13.7 mg of (ethyl)$_2$PN(methyl)P(ethyl)$_2$ (0.066 mmol) in 10 ml of methylcyclohexane was added to a solution of 11.7 mg Cr(acetylacetonate)$_3$ (0.033 mmol) in 10 ml methylcyclohexane in a Schlenk vessel. This solution was mixed with a solution of MMAO-3A (modified methylaluminoxane, 9.9 mmol) and immediately added to a 300 ml pressure reactor (autoclave) containing methylcyclohexane (70 ml) at 60° C. The pressure reactor was charged with ethylene after which the reactor temperature was controlled at 60° C., while the ethylene pressure was maintained at 5000 kPa. The reaction was terminated after 30 min, and the procedure of Example 1 above was employed. The product mass was 12.7 g. The product distribution of this example is summarised in Table 1.

Example 53

Ethylene Tetramerisation Reaction Using Cr(2-ethylhexanoate)$_3$, (ethyl)$_2$PN(isopropyl)P(phenyl)$_2$ and MAO in Toluene at 45° C./4000 kPa A solution of Cr(2-ethylhexanoate)$_3$ (0.002M in toluene, 10 ml, 0.02 mmol) and a solution of (ethyl)$_2$PN(isopropyl)P (phenyl)$_2$ (0.004M in toluene, 5 ml, 0.02 mmol) were added to a 300 ml pressure reactor (autoclave) containing a mixture of toluene (100 ml) and MAO (methylaluminoxane, 6.0 mmol) at 45° C. The pressure reactor was charged with ethylene after which the reactor temperature was controlled at 45° C., while the ethylene pressure was maintained at 4000 kPa. The reaction was terminated after 30 min, and the procedure of Example 1 above was employed. The product mass was 10.8 g. The product distribution of this example is summarised in Table 1.

Example 54

Ethylene Tetramerisation Reaction Using Cr(acetylacetonate)$_3$, (ethyl)$_2$PN(isopropyl)P(phenyl)$_2$ and MMAO-3A in Methylcyclohexane at 60° C./5000 kPa A solution of 21.8 mg of (ethyl)$_2$PN(isopropyl)P(phenyl)$_2$ (0.066 mmol) in 10 ml of methylcyclohexane was added to a solution of 11.7 mg Cr(acetylacetonate)$_3$ (0.033 mmol) in 10 ml methylcyclohexane in a Schlenk vessel. This solution was mixed with a solution of MMAO-3A (modified methylaluminoxane, 9.9 mmol) and immediately added to a 300 ml pressure reactor (autoclave) containing methylcyclohexane (70 ml) at 60° C. The pressure reactor was charged with ethylene after which the reactor temperature was controlled at 60° C., while the ethylene pressure was maintained at 5000 kPa. The reaction was terminated after 30 min, and the procedure of Example 1 above was employed. The product mass was 39.4 g. The product distribution of this example is summarised in Table 1.

Example 55

Ethylene Tetramerisation Reaction Using Cr(acetylacetonate)$_3$, (phenyl)$_2$PCH$_2$CH$_2$P(phenyl)$_2$ and MAO in Toluene at 45° C./4000 kPa A solution of 26.3 mg of (phenyl)$_2$PCH$_2$CH$_2$P(phenyl)$_2$ (0.066 mmol) in 10 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was controlled at 45° C., while the ethylene pressure was maintained at 4000 kPa. The reaction was terminated after 30 min, and the procedure of Example 1 above was employed. The product mass was 21.23 g. The product distribution of this example is summarised in Table 1.

Example 56

Ethylene Tetramerisation Reaction Using Cr(acetylacetonate)$_3$, (phenyl)$_2$PCH$_2$CH$_2$P(phenyl)$_2$ and MMAO-3A in Methylcyclohexane at 80° C./4000 kPa A solution of 26.3 mg of (phenyl)$_2$PCH$_2$CH$_2$P(phenyl)$_2$ (0.066 mmol) in 10 ml of methylcyclohexane was added to a solution of 11.7 mg Cr(acetylacetonate)$_3$ (0.033 mmol) in 10 ml methylcyclohexane in a Schlenk vessel. This solution was mixed with a solution of MAO (methylaluminoxane, 9.9 mmol) and immediately added to a 300 ml pressure reactor (autoclave) containing methylcyclohexane (70 ml) at 80° C.

The pressure reactor was charged with ethylene after which the reactor temperature was controlled at 80° C., while the ethylene pressure was maintained at 4000 kPa. The reaction was terminated after 30 min, and the procedure of Example 1 above was employed. The product mass was 50.6 g. The product distribution of this example is summarised in Table 1.

Example 57

Ethylene Tetramerisation Reaction Using Cr(acetylacetonate)$_3$, (phenyl)$_2$P(1,2-phenylene)P(phenyl)$_2$ and MAO in Toluene at 45° C./4500 kPa A solution of 29.4 mg of (phenyl)$_2$P(1,2-phenylene)P(phenyl)$_2$ (0.066 mmol) in 10 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (80 ml) and MAO (methylaluminoxane, 9.9 mmol) at 45° C. The pressure reactor was charged with ethylene after which the reactor temperature was controlled at 45° C., while the ethylene pressure was maintained at 4500 kPa. The reaction was terminated after 60 min, and the procedure of Example 1 above was employed. The product mass was 64.73 g. The product distribution of this example is summarised in Table 1.

Example 58

Ethylene Tetramerisation Reaction Using Cr(acetylacetonate)$_3$, (phenyl)$_2$P(1,2-phenylene)P(phenyl)$_2$ and MMAO-3A in Methylcyclohexane at 80° C./4000 kPa A solution of 26.3 mg of (phenyl)$_2$P(1,2-phenylene)P(phenyl)$_2$ (0.066 mmol) in 10 ml of methylcyclohexane was added to a solution of 11.7 mg Cr(acetylacetonate)$_3$ (0.033 mmol) in 10 ml methylcyclohexane in a Schlenk vessel. This solution was mixed with a solution of MAO (methylaluminoxane, 9.9 mmol) and immediately added to a 300 ml pressure reactor (autoclave) containing methylcyclohexane (70 ml) at 80° C. The pressure reactor was charged with ethylene after which the reactor temperature was controlled at 80° C., while the ethylene pressure was maintained at 4000 kPa. The reaction was terminated after 45 min, and the procedure of Example 1 above was employed. The product mass was 90.5. The product distribution of this example is summarised in Table 1.

Example 59.1

Preparation of the Complex {[(phenyl)$_2$P(1,2-phenylene)P(phenyl)$_2$]CrCl$_3$}$_2$ The complex {[(phenyl)$_2$P(1,2-phenylene)P(phenyl)$_2$]CrCl$_3$}$_2$ was prepared according to the synthesis of [(phenyl$_2$P)$_2$N(phenyl)CrCl$_3$]$_2$ as described in J. Am. Chem. Soc. 2004, 126(45), 14712.

Example 59

Ethylene Tetramerisation Reaction Using {[(phenyl)$_2$P(1,2-phenylene)P(phenyl)$_2$]CrCl$_3$}$_2$ and MAO in Toluene at 80° C./5000 kPa A suspension of 3.02 mg of {[(phenyl)$_2$P(1,2-phenylene)P(phenyl)$_2$]CrCl$_3$}$_2$ (0.0025 mmol) in 10 ml of methylcyclohexane was transferred to a 300 ml pressure reactor (autoclave) containing a mixture of methylcyclohexane (90 ml) and MMAO-3A (modified methylaluminoxane, 1 mmol) at 80° C. The pressure reactor was charged with ethylene after which the reactor temperature was controlled at 80° C., while the ethylene pressure was maintained at 5000 kPa. The reaction was terminated after 6 min, and the procedure of Example 1 above was employed. The product mass was 76.4 g. The product distribution of this example is summarised in Table 1.

Example 60

Ethylene Tetramerisation Reaction using {[(phenyl)$_2$P(1,2-phenylene)P(phenyl)$_2$]CrCl$_3$}$_2$ and MAO in Toluene at 100° C./5600 kPa A suspension of 6.04 mg of {[(phenyl)$_2$P(1,2-phenylene)P(phenyl)$_2$]CrCl$_3$}$_2$ (0.005 mmol) in 10 ml of methylcyclohexane was transferred to a 300 ml pressure reactor (autoclave) containing a mixture of methylcyclohexane (90 ml) and MMAO-3A (modified methylaluminoxane, 1.5 mmol) at 100° C. The pressure reactor was charged with ethylene after which the reactor temperature was controlled at 100° C., while the ethylene pressure was maintained at 5600 kPa. The reaction was terminated after 5.5 min, and the procedure of Example 1 above was employed. The product mass was 94.9 g. The product distribution of this example is summarised in Table 1.

Example 61

Ethylene Tetramerisation Reaction Using Cr(acetylacetonate)$_3$, (phenyl)$_2$PN(methyl)N(methylP(phenyl)$_2$ and MAO in Toluene at 45° C./4500 kPa A solution of 28.3 mg of (phenyl)$_2$PN(methyl)N(methylP(phenyl)$_2$ (0.066 mmol) in 15 ml of toluene was added to a solution of 11.5 mg Cr (acetylacetonate)$_3$ (0.033 mmol) in 10 ml toluene in a Schlenk vessel. The mixture was stirred for 5 min at ambient temperature and was then transferred to a 300 ml pressure reactor (autoclave) containing a mixture of toluene (75 ml) and MAO (methylaluminoxane, 9.9 mmol) at 40° C. The pressure reactor was charged with ethylene after which the reactor temperature was controlled at 45° C., while the ethylene pressure was maintained at 4500 kPa. The reaction was terminated after 30 min, and the procedure of Example 1 above was employed. The product mass was 22.5 g. The product distribution of this example is summarised in Table 1.

Example 62

Ethylene Tetramerisation Reaction Using Cr(acetylacetonate)$_3$, (phenyl)$_2$PN(methyl)N(methylP(phenyl)$_2$ and MMAO in Methylcyclohexane at 60° C./5000 kPa A solution of 2.23 mg of (phenyl)$_2$PN(methyl)N(methylP(phenyl)$_2$ (0.005 mmol) in 15 ml of methylcyclohexane was added to a solution of 1.7 mg Cr (acetylacetonate)$_3$ (0.005 mmol) in 10 ml methylcyclohexane in a Schlenk vessel. The mixture was stirred for 5 min at ambient temperature and was then transferred to a 300 ml pressure reactor (autoclave) containing a mixture of methylcyclohexane (80 ml) and MMAO-3A (modified methylaluminoxane, 1.5 mmol) at 55° C. The pressure reactor was charged with ethylene after which the reactor temperature was controlled at 60° C., while the ethylene pressure was maintained at 5000 kPa. The reaction was terminated after 35 min, and the procedure of Example 1 above was employed. The product mass was 63.1 g. The product distribution of this example is summarised in Table 1.

Example 63.1

Preparation of [(propyl$_2$PCH$_2$CH$_2$propyl$_2$)CrCl$_3$]$_2$

CrCl$_3$(THF)$_3$ (225 mg, 0.60 mmol) was suspended in THF (5 ml) and a THF (5 ml) solution of 1,2-bis(di-iso-propylphosphino)ethane (157 mg, 0.59 mmol) was added. Within 30 seconds the solution had turned navy blue and was allowed to stir overnight. The solvent was removed in vacuo leaving a dark blue solid which was washed with petroleum ether 40-60 until the washings were colourless. The powder was dried in vacuo to give the title complex (128 mg, 50%). Calcd. for C$_{28}$H$_{64}$Cl$_6$Cr$_2$P$_4$ (found): C 39.67 (39.97), H 7.93 (7.67).

Example 63

Ethylene Tetramerisation Reaction Using [(propyl$_2$PCH$_2$CH$_2$propyl$_2$)CrCl$_3$]$_2$ and MAO in Toluene at 45° C./4000 kPa A suspension of 33.4 mg of [(propyl$_2$PCH$_2$CH$_2$propyl$_2$)CrCl$_3$]$_2$ (0.04 mmol) in 20 ml of toluene was transferred to a 300 ml pressure reactor (autoclave) containing a mixture of toluene (80 ml) and MAO (methylaluminoxane, 12.0 mmol) at 55° C. The pressure reactor was charged with ethylene after which the reactor temperature was controlled at 60° C., while the ethylene pressure was maintained at 4000 kPa. The reaction was terminated after 30 min, and the procedure of Example 1 above was employed. The product mass was 11.5 g. The product distribution of this example is summarised in Table 1.

Example 64

Ethylene Tetramerisation Reaction Using [(propyl$_2$PCH$_2$CH$_2$propyl$_2$)CrCl$_3$]$_2$ and MAO in Cyclohexane at 45° C./4000 kPa A suspension of 16.7 mg of [(propyl$_2$PCH$_2$CH$_2$propyl$_2$)CrCl$_3$]$_2$ (0.02 mmol) in 20 ml of cyclohexane was transferred to a 300 ml pressure reactor (autoclave) containing a mixture of cyclohexane (80 ml) and MAO (methylaluminoxane, 6.0 mmol) at 55° C. The pressure reactor was charged with ethylene after which the reactor temperature was controlled at 60° C., while the ethylene pressure was maintained at 4000 kPa. The reaction was terminated after 30 min, and the procedure of Example 1 above was employed. The product mass was 9.6 g. The product distribution of this example is summarised in Table 1.

TABLE 1

| Ex. | Solvent | T °C. | P kPa | activity g/g Cr/h | C-6 % | 1-hex. % | C-8 % | 1-oct. % |
|---|---|---|---|---|---|---|---|---|
| 1 | Toluene | 45 | 4500 | 285900 | 25.4 | 69.9 | 69 | 99 |
| 2 | Ethylbenzene | 45 | 4500 | 384600 | 16.4 | 70.9 | 71.4 | 99 |
| 3 | o-Xylene | 45 | 4500 | 198300 | 18.2 | 69.5 | 71.1 | 98.9 |
| 4 | p-Xylene | 45 | 4500 | 132800 | 18.4 | 79.1 | 69.9 | 99 |
| 5 | m-Xylene | 45 | 4500 | 292900 | 16.4 | 67 | 68.1 | 98.9 |
| 6 | Diethylbenzene | 45 | 4500 | 380100 | 28.2 | 69 | 61.8 | 98.9 |
| 7 | Cumene | 45 | 4500 | 234600 | 16 | 67.7 | 69.4 | 98.8 |
| 8 | Cumene | 60 | 4500 | 88600 | 21.7 | 79.3 | 68.9 | 99.1 |
| 9 | Toluene | 85 | 3000 | 16500 | 34.1 | 92.7 | 33.7 | 98.9 |
| 10 | Toluene | 85 | 3000 | 12900 | 36.6 | 74.5 | 55.5 | 97.5 |
| 11 | Cyclohexane | 60 | 4500 | 720200 | 20 | 77.2 | 65.6 | 99 |
| 12 | Cyclohexane | 60 | 4500 | 948200 | 18.4 | 74 | 66.2 | 98.9 |
| 13 | Isopar C | 65 | 4500 | 580200 | 20 | 76.7 | 68.1 | 99.1 |
| 14 | Isopar E | 60 | 4500 | 987800 | 20.7 | 70.3 | 66.7 | 89.8 |
| 15 | C7-C8 n-Paraffins | 60 | 4500 | 484800 | 19 | 76.2 | 67.3 | 99.1 |
| 16 | Methylcyclohexane | 80 | 4500 | 354100 | 31.3 | 87.8 | 56.9 | 98.7 |
| 17 | Methylcyclohexane | 60 | 4500 | 1220000 | 19.3 | 76.4 | 65.9 | 99.0 |
| 18 | Methylcyclohexane +2 ml toluene | 60 | 4500 | 654500 | 18 | 75.5 | 68.2 | 99.0 |
| 19 | Methylcyclohexane | 80 | 8000 | 928800 | 24.5 | 79.7 | 66.4 | 99.0 |
| 20 | Methylcyclohexane | 60 | 8000 | 573800 | 16.8 | 69.4 | 74.2 | 98.8 |
| 21 | Methylcyclohexane | 100 | 5000 | 687200 | 45.2 | 94 | 37.5 | 98.8 |
| 22 | Toluene | 45 | 4500 | 66100 | 22.7 | 60.5 | 68.2 | 98.9 |
| 23 | Methylcyclohexane | 60 | 7000 | 6202800 | 21.7 | 82.9 | 66.3 | 99.4 |
| 24 | Methylcyclohexane | 80 | 5000 | 1718700 | 41.6 | 94.5 | 48.9 | 99.6 |
| 25 | Toluene | 60 | 5000 | 16600 | 25.4 | 87.5 | 58.5 | 98.6 |
| 26 | Methylcyclohexane | 60 | 7000 | 2679300 | 24.8 | 83.6 | 64.4 | 99.4 |
| 27 | Methylcyclohexane | 80 | 5000 | 323000 | 44.4 | 95.3 | 41.2 | 99.3 |
| 28 | Toluene | 45 | 3000 | 8300 | 26.8 | 83.1 | 69.1 | 99.5 |
| 29 | Methylcyclohexane | 80 | 5700 | 993000 | 35.6 | 91.9 | 52.5 | 98.8 |
| 30 | Methylcyclohexane | 60 | 4500 | 424000 | 20.2 | 79.3 | 64.9 | 99.1 |
| 31 | Toluene | 45 | 4500 | 288600 | 17.2 | 68.8 | 67.8 | 98.9 |
| 32 | Toluene | 85 | 3000 | 8540 | 31.6 | 83 | 45.3 | 98 |
| 33 | Methylcyclohexane | 60 | 5000 | 765900 | 16.6 | 54.2 | 61.8 | 97.1 |
| 34 | Toluene | 65 | 3000 | 4500 | 18.9 | 75 | 36.5 | 97.1 |
| 35 | Toluene | 85 | 3000 | 6070 | 20 | 84.4 | 29.2 | 97.6 |
| 36 | Methylcyclohexane | 60 | 5000 | 932800 | 14.8 | 53.5 | 53.3 | 96.9 |
| 37 | Toluene | 65 | 3000 | 12000 | 26.6 | 67.2 | 61.8 | 97.8 |
| 38 | Toluene | 85 | 3000 | 5150 | 35.2 | 82.4 | 48.7 | 98.1 |
| 39 | Methylcyclohexane | 60 | 5000 | 1147200 | 17.7 | 53.5 | 62.3 | 96.9 |
| 40 | Toluene | 65 | 3000 | 4300 | 28 | 61.7 | 60.2 | 98.1 |
| 41 | Toluene | 85 | 3000 | 6680 | 42.1 | 80 | 43.4 | 98.1 |
| 42 | Methylcyclohexane | 60 | 5000 | 1065300 | 18.8 | 46.5 | 63.5 | 97.2 |
| 43 | Toluene | 65 | 3000 | 30800 | 22.9 | 38.6 | 56.1 | 95.3 |
| 44 | Methylcyclohexane | 65 | 5000 | 50300 | 14.2 | 38 | 40 | 94.3 |
| 45 | Toluene | 65 | 3000 | 45200 | 26 | 46.6 | 50.1 | 93.5 |
| 46 | Methylcyclohexane | 60 | 3000 | 175300 | 28.3 | 54.7 | 53.4 | 94.7 |
| 47 | Toluene | 45 | 4500 | 61800 | 93 | 99.6 | 6.4 | >99.9 |
| 48 | Methylcyclohexane | 55 | 2000 | 3524400 | 89.9 | 99.8 | 2.2 | >99.9 |
| 49 | Toluene | 45 | 4500 | 159600 | 82.2 | 99.7 | 13 | >99.9 |
| 50 | Methylcyclohexane | 90 | 3500 | 2381800 | 88.4 | 98.6 | 2.1 | 98.6 |
| 51 | Toluene | 45 | 4000 | 4400 | 16.8 | 64.6 | 45.2 | 97.4 |
| 52 | Methylcyclohexane | 60 | 5000 | 14800 | 40.5 | 84.9 | 40.3 | 96.3 |
| 53 | Toluene | 45 | 4000 | 20800 | 20.2 | 69.0 | 69.0 | 99.6 |
| 54 | Methylcyclohexane | 60 | 5000 | 46000 | 16.9 | 62.3 | 74.0 | 98.4 |
| 55 | Toluene | 45 | 4000 | 24800 | 19.7 | 38.2 | 39.2 | 96.6 |
| 56 | Methylcyclohexane | 80 | 4000 | 62800 | 39.5 | 76.9 | 29.3 | 98.0 |
| 57 | Toluene | 45 | 4500 | 37700 | 28.8 | 36.3 | 31.1 | 94.8 |
| 58 | Methylcyclohexane | 80 | 4000 | 70500 | 39.4 | 75.9 | 43.6 | 97.8 |
| 59 | Methylcyclohexane | 80 | 5000 | 5876000 | 39.0 | 72.7 | 51.8 | 97.5 |
| 60 | Methylcyclohexane | 100 | 5600 | 3985000 | 48.1 | 86.4 | 34.2 | 98.0 |
| 61 | Toluene | 45 | 4500 | 26200 | 25.2 | 69.6 | 58.8 | 98.4 |

TABLE 1-continued

| | | | | | | | |
|---|---|---|---|---|---|---|---|
| 62 Methyl-cyclohexane | 60 | 5000 | 416000 | 30.8 | 83.7 | 60.9 | 99.4 |
| 63 Toluene | 60 | 4000 | 11100 | 88.9 | 99.1 | 5.7 | >99.9 |
| 64 Cyclohexane | 60 | 4000 | 18400 | 89.0 | 99.8 | 6.0 | >99.9 |

% are mass percentages

A comparison of the results of Examples 1-10 (all catalytic runs in a variety of aromatic solvents) with Examples 11-17, 19-20 and 30-31 (all runs in a variety of aliphatic solvents) indicates that, irrespective of the aromatic solvent employed, all catalytic runs with the Cr(acetylacetonate)$_3$/(phenyl)$_2$PN (isopropyl)P(phenyl)$_2$/aluminoxane catalyst system in aliphatic solvents exhibited significantly higher reaction rates. This trend is also evident when a chromium coordination complex containing the same ligating compound is employed (see Example 21). In fact, comparing Example 18 with Example 17 indicates that the presence of only 1 volume % toluene in methylcyclohexane resulted in a nearly 50 reduction on reaction rate.

The positive influence of aliphatic solvents on both reaction rate and catalyst stability is particularly apparent in FIG. 1 which shows the cumulative ethylene uptake curves for Examples 8 and 12. In the case of Example 8 (a catalytic run in cumene, an aromatic solvent), the ethylene uptake rate decreased significantly over the first 500 seconds of run time while in the case of Example 12 (a catalytic run in cyclohexane, an aliphatic solvent) the ethylene uptake rate increased gradually over the first 1500 seconds of run time with no visible signs of catalyst deactivation thereafter.

Examples 22-29 and 32-64 indicate that this phenomenon is applicable to a variety of olefin oligomerisation catalyst systems (the catalytic runs in aliphatic solvents always exhibited significantly higher rates).

The invention claimed is:

1. A process for producing an oligomeric product containing octene by the tetramerisation of an olefinic compound in the form of ethylene comprising contacting ethylene with a tetramerisation catalyst in an aliphatic liquid medium at a reaction temperature of at least 50° C., wherein the catalyst comprises the combination of
   i) a source of a transition metal; and
   ii) a ligating compound of the formula

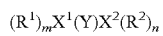
   $(R^1)_mX^1(Y)X^2(R^2)_n$ wherein:
   $X^1$ and $X^2$ are independently selected from the group consisting of
   N, P, As, Sb, Bi, O, S and Se;
   Y is a linking group between $X^1$ and $X^2$;
   m and n are independently 0, 1 or a larger integer; and
   $R^1$ and $R^2$ are independently hydrogen, a hydrocarbyl group or a heterohydrocarbyl group, and $R^1$ is the same or different when m>1, and $R^2$ is the same or different when n>1 and
   wherein the product produced includes more than 30% by mass of octene.

2. The process of claim 1 wherein the product comprises a mixture of hexene and octene.

3. The process of claim 1 or 2 wherein the aliphatic liquid medium comprises at least one acyclic compound.

4. The process of claim 1 or 2 wherein the aliphatic liquid medium comprises a cyclic compound.

5. The process of claim 4 wherein the cyclic compound is a saturated cyclic hydrocarbon.

6. The process of claim 5 wherein the ring structure defined by the saturated cyclic hydrocarbon consists of 3 to 12 carbon atoms.

7. The process of claim 6 wherein the aliphatic liquid medium comprises cyclohexane.

8. The process of claim 6 wherein the aliphatic liquid medium comprises a substituted cyclohexane wherein a hydrogen atom of cyclohexane is substituted with a substitution moiety which is not H.

9. The process of claim 8 wherein the substitution moiety comprises an organyl.

10. The process of claim 9 wherein the aliphatic liquid medium comprises methylcyclohexane.

11. The process of claim 1 wherein the reaction temperature is at least 60° C.

12. The process of claim 1 wherein the reaction is carried out at a pressure above 1000 kPa.

13. The process of claim 12 wherein the pressure is at least 4500 kPa.

14. The process of claim 1 which includes one or more activators.

15. The process of claim 14 which includes an activator in the form of an aluminium compound.

16. The process of claim 15 wherein the activator is an alkylaluminoxane.

17. The process of claim 16 wherein the alkylaluminoxane is selected from the group consisting of methylaluminoxane, high stability methylaluminoxane, ethylaluminoxane, isobutylaluminoxane and modified methylaluminoxane.

18. The process of claim 17 wherein the alkylaluminoxane is modified methylaluminoxane.

19. The process of claim 1 wherein the source of transition metal is a source of a Group IV to VI transition metal.

20. The process of claim 19 wherein the transition metal is a source of Cr.

21. The process of claim 1 wherein the ligating compound is of the formula

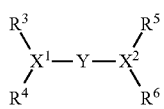

$X^1$ and $X^2$ are independently selected from the group consisting of N, P, As, Sb and Bi; and $R^3$ to $R^6$ are each independently a hydrocarbyl group or a heterohydrocarbyl group.

22. The process of claim 21 wherein both $X^1$ and $X^2$ are P.

23. The process of either one of claim 21 or 22 wherein each of $R^3$ to $R^6$ does not have any polar substituent and at least two of $R^3$ to $R^6$ are aromatic with a ring atom of the aromatic ring structure bound to $X^1$ or $X^2$, but not more than two of said aromatic $R^3$ to $R^6$ have a non-polar substituent as a non-ring atom bound to a ring atom of the aromatic ring structure adjacent to the ring atom bound to $X^1$ or $X^2$.

24. The process of claim 23 wherein all of $R^3$ to $R^6$ are aromatic and none of the aromatic $R^3$ to $R^6$ have a non-polar substituent as a non-ring atom bound to a ring atom of the aromatic ring structure adjacent to the ring atom bound to $X^1$ or $X^2$.

25. The process of either one of claim 21 or 22 wherein $R^3$ to $R^6$ are the same or different and each is a hydrocarbyl group, or a heterohydrocarbyl group, provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$.

26. The process of claim 1 wherein Y is selected from the group consisting of an organic linking group; an inorganic linking group; methylene; dimethylmethylene; 1,2-ethane; 1,2-ethene; 1,1-cyclopropane, 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol; 1,2-dialkylhydrazine; —B($R^7$)—, —Si($R^7$)$_2$—, —P($R^7$)— and —N($R^7$)— where $R^7$ is hydrogen, a hydrocarbyl or heterocarbyl or halogen.

27. The process of claim 26 wherein Y is N($R^7$)— and $R^7$ is a hydrocarbyl or a substituted hydrocarbyl group.

28. The process of claim 26, wherein the organic linking group is a hydrocarbyl, a substituted hydrocarbyl, a heterohydrocarbyl or a substituted heterohydrocarbyl group and the inorganic linking group is a single atom link bound to $X^1$ and $X^2$.

* * * * *